United States Patent
Birkle et al.

(10) Patent No.: US 10,745,489 B2
(45) Date of Patent: Aug. 18, 2020

(54) **TARGETING O-ACETYLATED GD2 GANGLIOSIDE AS A NEW THERAPEUTIC AND DIAGNOSTIC STRATEGY FOR *CANCER STEM CELLS* CANCER**

(71) Applicants: OGD2 PHARMA, Nantes (FR); UNIVERSITE DE NANTES, Nantes (FR)

(72) Inventors: Stephane Birkle, Nantes (FR); Denis Cochonneau, Nantes (FR); Mylene Dorvillius, Nantes (FR); Jean-Marc Le Doussal, Nantes (FR); Mickael Terme, Nantes (FR)

(73) Assignees: OGD2 PHARMA, Nantes (FR); UNIVERSITE DE NANTES, Nantes (FR)

(*) Notice: Subject to any disclaimer, the term of this patent is extended or adjusted under 35 U.S.C. 154(b) by 0 days.

(21) Appl. No.: 15/984,980

(22) Filed: May 21, 2018

(65) Prior Publication Data
US 2019/0023808 A1 Jan. 24, 2019

Related U.S. Application Data

(63) Continuation-in-part of application No. 14/787,707, filed as application No. PCT/EP2014/001142 on Apr. 29, 2014, now Pat. No. 10,000,575.

(30) Foreign Application Priority Data

Apr. 29, 2013 (EP) .................................... 13002268

(51) Int. Cl.
| | |
|---|---|
| *A61P 35/00* | (2006.01) |
| *G01N 33/574* | (2006.01) |
| *C07K 16/30* | (2006.01) |
| *C07K 16/28* | (2006.01) |
| *G01N 33/92* | (2006.01) |
| *A61K 39/00* | (2006.01) |

(52) U.S. Cl.
CPC .......... *C07K 16/3084* (2013.01); *A61P 35/00* (2018.01); *C07K 16/289* (2013.01); *C07K 16/2863* (2013.01); *C07K 16/2884* (2013.01); *G01N 33/57407* (2013.01); *G01N 33/92* (2013.01); *A61K 2039/505* (2013.01); *C07K 2317/73* (2013.01); *G01N 2400/00* (2013.01); *G01N 2440/10* (2013.01)

(58) Field of Classification Search
CPC . C71K 16/3084; A61P 35/00; C07K 16/2863; C07K 16/2884; C07K 16/289; G01N 33/574
USPC ..................................................... 424/137.1
See application file for complete search history.

(56) References Cited

U.S. PATENT DOCUMENTS

| | | |
|---|---|---|
| 5,225,539 A | 7/1993 | Winter |
| 5,585,089 A | 12/1996 | Queen et al. |
| 5,730,969 A | 3/1998 | Hora et al. |
| 8,951,524 B2 | 2/2015 | Birkle |
| 9,334,330 B2 | 5/2016 | Birkle |
| 2006/0258852 A1 | 11/2006 | Lugovskoy et al. |
| 2010/0150910 A1 | 6/2010 | Birkle et al. |

FOREIGN PATENT DOCUMENTS

| | | |
|---|---|---|
| FR | 2 906 808 | 4/2008 |
| GB | 2 188 638 | 10/1987 |
| WO | 2009036099 | 3/2009 |
| WO | 2010011893 | 1/2010 |

OTHER PUBLICATIONS

D. Cochonneau et al.: "Cell cycle arrest and apoptosis induced by O-acetyl-GD2-specific monoclonal antibody 8B6 inhibits tumor growth in vitro and in vivo.", Cancer Letters, vol. 333, No. 2, Jan. 28, 2013 (Jan. 28, 2013), pp. 194-204, XP028581871.
N. Alvarez-Rueda et al.: "A monoclonal antibody to O-acetyl-GD2 ganglioside and not to GD2 shows potent anti-tumor activity without peripheral nervous system cross-reactivity.", PLOS ONE, vol. 6, No. 9, E25220, Sep. 2011 (Sep. 2011), pp. 1-12, XP002728103.
A. Mezazigh et al.: "A monoclonal antibody reacting specifically for ganglioside O-acetylated GD2 in neuroectodermal tumors.", Glycoconjugate Journal, vol. 10, No. 4, Aug. 20, 1993 (Aug. 20, 1993), pp. 300-301, XP008078472.
J. Nautiyal et al.: "Combination of dasatinib and curcumin eliminates chemo-resistant colon cancer cells.", Journal of Molecular Signaling, vol. 6, No. 1, Jul. 20, 2011 (Jul. 20, 2011), p. 7, XP021105972.
International Search Report, dated Aug. 19, 2014, from corresponding PCT Application.
Alvarez-Rueda et al. (PLoS ONE, vol. 6, No. 9, Sep. 2011, p. e25220).
Harmsen and Haard (Appl Microbiol Biotechnol 2007, 77:13-22).
Cheever et al. (Clin Cancer Res 2009,15(17): 5323-37).

*Primary Examiner* — Yan Xiao
(74) *Attorney, Agent, or Firm* — Young & Thompson

(57) ABSTRACT

An antibody recognizing the O-acetylated-GD2 ganglioside for the treatment of Cancer Stem Cells (CSC) cancer, a pharmaceutical composition including the antibody for treating a CSC cancer and a method for treating a CSC cancer in a patient in need thereof, the method including administering the antibody to the patient. A method for diagnosing a CSC, the use of the O-acetylated-GD2 ganglioside as a biomarker of CSC cancer, and a method for predicting the response of a subject affected with CSC cancer to a treatment with the antibody or the composition are also described.

12 Claims, 7 Drawing Sheets
Specification includes a Sequence Listing.

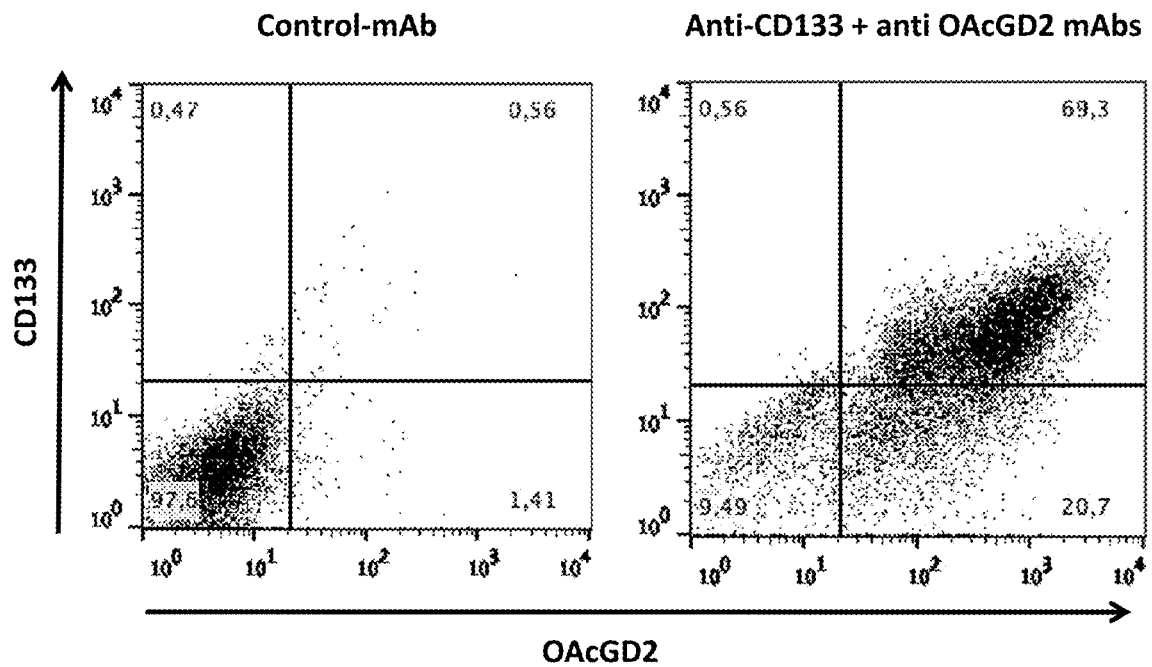
Figure 7-A
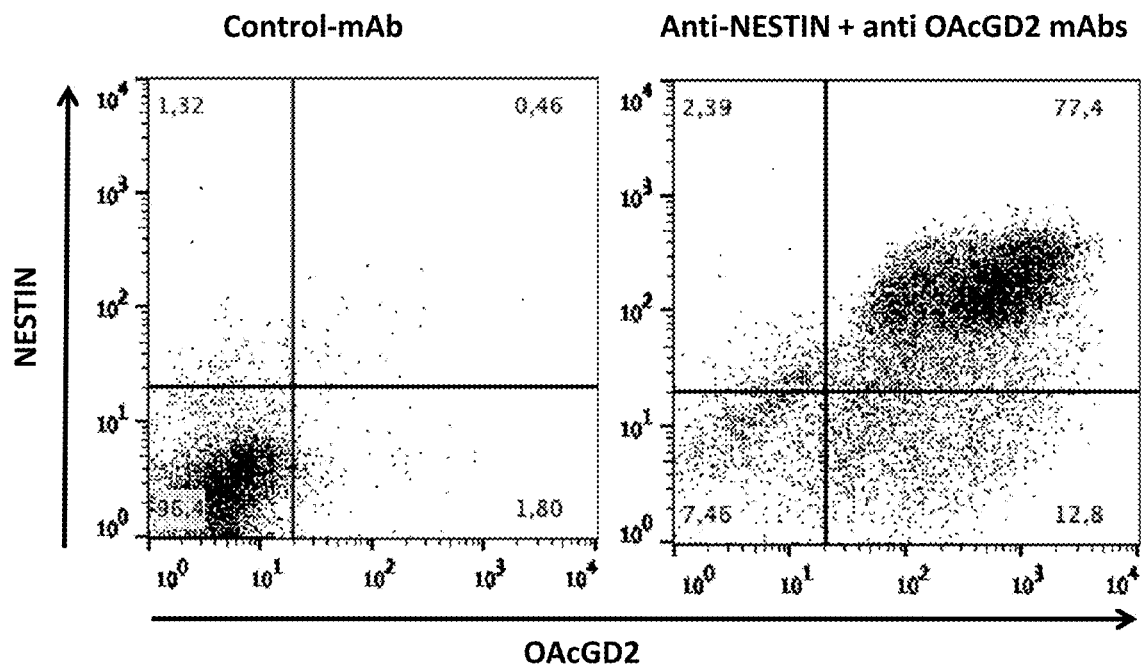
Figure 7-B

TARGETING O-ACETYLATED GD2 GANGLIOSIDE AS A NEW THERAPEUTIC AND DIAGNOSTIC STRATEGY FOR *CANCER STEM CELLS* CANCER

This application is a continuation-in-part of U.S. application Ser. No. 14/787,707, which was the National Stage of International Application No. PCT/EP2014/001142, filed Apr. 29, 2014, which claimed the priority of the European patent application 13002268.4 filed on Apr. 29, 2014, which is incorporated herein by reference.

FIELD OF THE INVENTION

The present invention relates to antibodies, pharmaceutical compositions, and methods for treating and/or diagnosing Cancer Stem Cells (CSC) cancer.

BACKGROUND OF THE INVENTION

Cancer Stem Cells

Advances in medical research these last decades permitted to importantly improve the existing cancer therapy strategies. In a parallel to the perpetual study and adaptation of the conventional therapeutic strategies including chemotherapy, radiotherapy, hormonal therapy and surgery, new cancer management approaches commonly called "targeted anti-cancer therapies" appeared and showed their efficiency and their interest in the medical world. These targeted therapies include monoclonal antibodies directed against tumor antigens such as trastuzumab (anti-Her2Neu), rituximab (anti-CD20) or bevacizumab (anti-VEGF), but also tyrosine kinase inhibitors (for example Imatinib, Erlotinib, Gefitinib), CDK inhibitors, etc. These new cancer treatment solutions largely improved the life of patients with increased survival rate and decreased side effects compared to more conventional strategies. However, these targeted therapy strategies also rapidly show limits, particularly due to resistance to said treatments, but also to the specificity of these targeted therapies, which are not efficient in every kind of cancers and patients. These resistance phenomena lead to treatment failure, appearance of metastases, relapses and recurrences.

Studies have shown that the root of these resistances might be the presence of cancer stem cells (CSC), a small subset of cancer cells that have the ability to self-renew and differentiate, and play a primordial role in cancer recalcitrance, recurrence and metastasis. Indeed, these cancer stem cells display relative resistance to cancer treatments, including radiation and chemotherapy. Furthermore, only a small amount of these cancer stem cells is sufficient to initiate a new tumor, and thus metastasis. Therefore, a direct targeting of these cancer stem cells may improve the efficacy of current cancer therapy strategies.

Cancer stem cells and associated mechanisms have thus been largely studied. Methods for identifying such cancer stem cells have been investigated, and few CSC markers were found. Unfortunately, there is still no antigen identified as CSC marker which is useful on many tumor types. Examples of currently used CSC markers include ALDH, CD133, CD44, CD24, CD166. Many different phenotypes have been identified as CSC phenotypes in different kind of cancers. Particularly, CD133, which is now widely used as a marker of cancer stem cells, appeared to be a good CSC marker in glioma.

Today, cell phenotype $CD133^+$ is related to cancer stem cell in glioma; phenotype $CD44^+CD24^{-/low}$ appears to be related to cancer stem cell in breast cancer; phenotype $CD34^+$ appears to be related to cancer stem cell in leukemia, more particularly $CD34^+/CD38$ is related to cancer stem cell in acute myeloid leukemia and phenotype $CD34^+/CD19^+$ appears to be related to cancer stem in acute lymphoid leukemia.

Unfortunately, most of known CSC markers are also expressed in some normal tissues. So, it would be of major interest to identify specific cancer markers that could be used as diagnostic and therapeutic CSC marker: they could be targeted for diagnosing, but also for treating cancers comprising cancer stem cells, herein called Cancer Stem Cells cancer (CSC cancer), without major side effects due to toxicity on healthy cells.

SUMMARY OF THE INVENTION

The inventors already showed that cancers of neuroectodermal origin specifically express the GD2-O-acetylated ganglioside and that a therapeutic antibody targeting GD2-O-acetylated ganglioside can be administrated and show beneficial effects without neurotoxicity, especially due to the absence of expression of this cancer antigen on healthy cells, notably on peripheral nerves.

Now and surprisingly, the inventors show that the GD2-O-acetylated ganglioside's expression is enriched on cancer stem cells, and could be targeted for CSC cancer treatment.

The inventors thus propose to target the O-acetylated-GD2 ganglioside for the treatment of CSC cancer, using the 8B6 antibody (and its derivatives) which is specific of the O-acetylated-GD2 ganglioside.

In their studies, they demonstrate that this antibody shows an intrinsic potent cytotoxic activity against tumor cells, including direct cytotoxicity to cancer stem cells through apoptosis or other cell death pathways, in addition to immune effects including CDC and ADCC.

Thus, the present invention relates to an antibody recognizing the O-acetylated-GD2 ganglioside, or a functional fragment thereof, for the treatment of Cancer Stem Cells (CSC) cancer, said antibody comprising:
  a) A light chain comprising at least a light chain variable region framework from an immunoglobulin and three complementary determining regions defined by the sequences SEQ ID NO:1 for CDR-L1, SEQ ID NO:2 for CDR-L2, SEQ ID NO:3 for CDR-L3, and/or
  b) An heavy chain comprising at least a heavy chain variable region framework from an immunoglobulin and three complementary determining regions defined by the sequences SEQ ID NO:4 for CDR-H1, SEQ ID NO:5 for CDR-H2, SEQ ID NO:6 for CDR-H3.

The invention also relates to a pharmaceutical composition for treating CSC cancer, said pharmaceutical composition comprising an antibody of the invention.

The present invention further relates to a method for diagnosing a CSC cancer in a subject, wherein said method comprises determining the expression of the O-acetylated-GD2 ganglioside, and wherein an expression of the O-acetylated-GD2 ganglioside is indicative of a CSC cancer. In an alternative embodiment, the diagnostic method comprises, detecting whether OAcGD2 is present on cancer stem cells by contacting the biological sample with an antibody that specifically binds to the O-acetylated-ganglioside (OAcGD2), wherein said anti-OAcGD2 antibody comprises a heavy chain variable region comprising SEQ ID NO:7 and a light chain variable region comprising SEQ ID NO:8, and detecting binding between OAcGD2 and the antibody that specifically binds to the OAcGD2.

The present invention also relates to a method of detecting O-acetylated-GD2 ganglioside in a subject suspected of having a cancer stem cell cancer, wherein said method comprises detecting whether OAcGD2 is coexpressed with at least one CSC biomarker.

The invention also relates to the use of the O-acetylated-GD2 ganglioside as a biomarker of CSC cancer.

The invention relates to a method for predicting the response of a subject affected with CSC cancer to a treatment with an antibody or a composition of the invention, wherein said method comprises detecting the presence of cells expressing the O-acetylated-GD2 ganglioside in a biological sample of said subject.

The invention finally relates to a kit for diagnosing a cancer stem cell cancer, wherein said kit comprises an anti-OAcGD2 antibody comprising a heavy chain variable region comprising SEQ ID NO:7 and a light chain variable region comprising SEQ ID NO:8 and instruction for use.

DESCRIPTION OF DRAWINGS

FIG. 7A and FIG. 7B: Expression of OAcGD2 in CSC of glioblastoma patient-derived cells. FACS analysis of CD133 (FIG. 7A) or Nestin (FIG. 7B) simultaneously with OAcGD2. The percentage of cells in each quadrant is indicated.

DETAILED DESCRIPTION OF THE INVENTION

Therapeutic Strategies of the Invention

Figure 1:
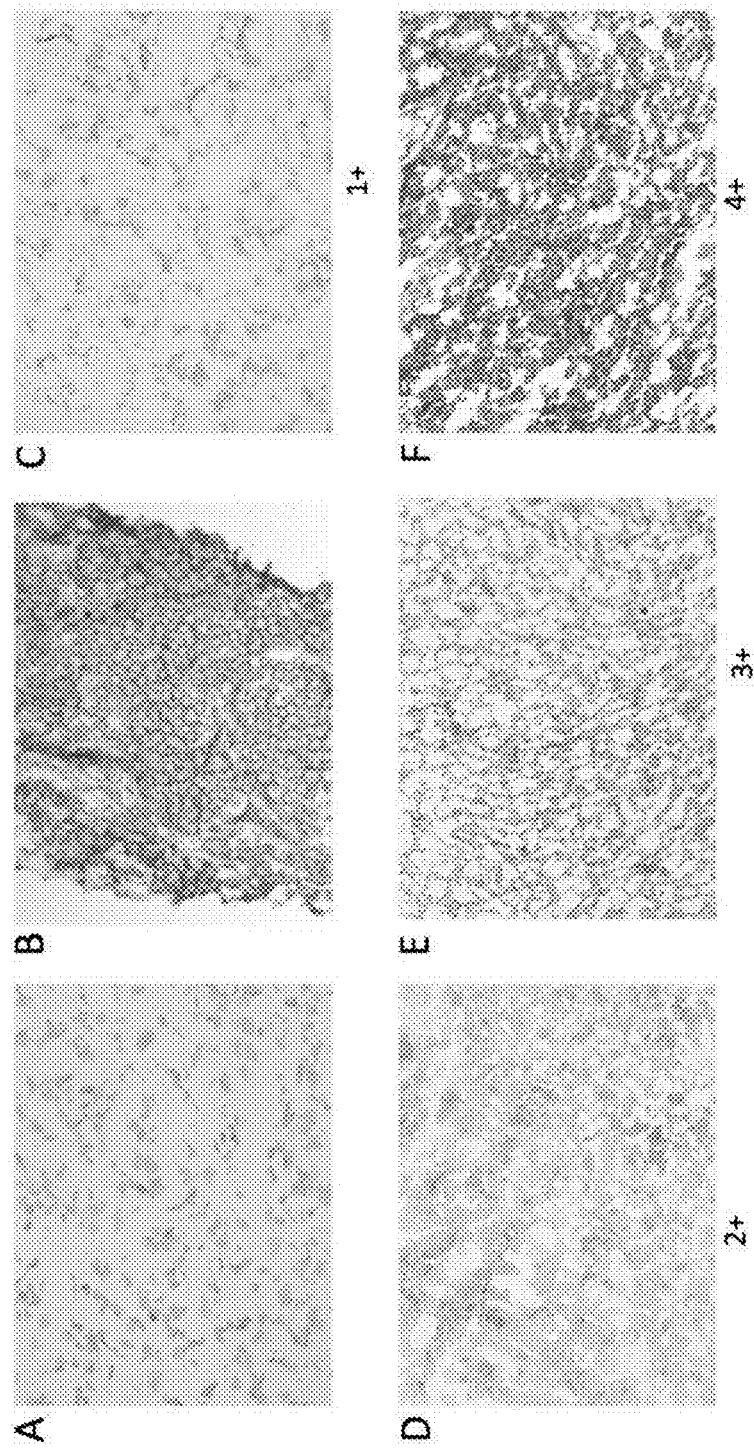
FIG. 1: Representative pictures of glioblastoma tumor section stained with mAb 8B6 (B). Glioblastoma tumor samples were scored 1+ (C), 2+ (D), 3+ (E), and 4+ (E) according to the specific intensity mAb 8B6 staining.

The first object of the invention relates to an antibody recognizing the O-acetylated-GD2 ganglioside, or a functional fragment thereof, for the treatment of Cancer Stem Cells (CSC) cancer, said antibody comprising:
  a) A light chain comprising at least a light chain variable region framework from an immunoglobulin and three complementary determining regions (CDRs) defined by the sequences SEQ ID NO:1 for CDR-L1, SEQ ID NO:2 for CDR-L2, SEQ ID NO:3 for CDR-L3, and/or
  b) An heavy chain comprising at least a heavy chain variable region framework from an immunoglobulin and three complementary determining regions (CDRs) defined by the sequences SEQ ID NO:4 for CDR-H1, SEQ ID NO:5 for CDR-H2, SEQ ID NO:6 for CDR-H3.

| | |
|---|---|
| SEQ ID NO: 1 | QSLLKNNGNTFL |
| SEQ ID NO: 2 | KVS |
| SEQ ID NO: 3 | SQSTHIPYT |
| SEQ ID NO: 4 | EFTFTDYY |
| SEQ ID NO: 5 | IRNRANGYTT |
| SEQ ID NO: 6 | ARVSNWAFDY |

Said CDRs are defined according to the IMGT nomenclature, which is well known in the art (The International Immunogenetics Information System®, LEFRANC et al., Nucleic Acids Research, vol. 27, p: 209-212, 1999).

The term "antibody" as its general meaning in the art and refers to an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a N-term heavy chain variable region (abbreviated herein as HCVR) and a heavy chain constant region. The heavy chain constant region is comprised of three domains (CH1, CH2, and CH3) and a Hinge region for IgG, IgD, and IgA; and 4 domains (CH1, CH2, CH3, and CH4) for IgM and IgE. Each light chain is comprised of an N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions. The functional ability of the antibody to bind a particular antigen depends on the variable regions of each light/heavy chain pair, and is largely determined by the CDRs.

In a particular embodiment, the antibody of the invention comprises:
  a) A light chain comprising a light chain framework from an immunoglobulin light chain and three complementary determining regions (CDRs) defined by the sequences SEQ ID NO:1 for CDR-L1, SEQ ID NO:2 for CDR-L2, SEQ ID NO:3 for CDR-L3, and/or
  b) An heavy chain comprising a heavy chain framework from an immunoglobulin heavy chain and three complementary determining regions (CDRs) defined by the sequences SEQ ID NO:4 for CDR-H1, SEQ ID NO:5 for CDR-H2, SEQ ID NO:6 for CDR-H3.

In a more particular embodiment, the antibody of the invention comprises a light chain variable region (LCVR) comprising the amino acid sequence SEQ ID NO:7 and a heavy chain variable region (HCVR) comprising the amino acid sequence SEQ ID NO:8. Said antibody is the 8B6 antibody.

| SEQ ID NO: 7 | DVVMTQTPLS | LPVSLGDQAS | ISCRSSQSLL | KNNGNTFLHW |
|---|---|---|---|---|
| | YLQKSGQSPK | LLIYKVSNRL | SGVPDRFSGS | GSGTYFTLKI |
| | SRVEAEDLGV | YFCSQSTHIP | YTFGGGTKLE | IK |
| SEQ ID NO: 8 | EVKLVESGGG | LVLPGDSLRL | SCATSEFTFT | DYYMTWVRQP |
| | PRKALEWLGF | IRNRANGYTT | EYNPSVKGRF | TISRDNSQSI |
| | LYLQMNTLRT | EDSATYYCAR | VSNWAFDYWG | QGTTLTVSS |

The term "antibody", as used herein, refers to a monoclonal antibody per se. A monoclonal antibody can be a human antibody, chimeric antibody and/or humanized antibody.

The term "functional fragment" as used herein refers to an antibody fragment capable of recognizing the O-acetylated-GD2 ganglioside. Such fragments can be simply identified or produced by the skilled person and comprise, as an example, $F_{ab}$ fragment (that can be produced by papain digestion), $F_{ab}'$ fragment (that can be produced by pepsin digestion and partial reduction), $F(_{ab}')_2$ fragment (that can be produced by pepsin digestion), $F_{acb}$, (that can be produced by plasmin digestion), $F_d$ (that can be produced by pepsin digestion, partial reduction and reaggregation), but also $scF_v$ (single chain Fv, produced by molecular biology techniques) fragment, diabodies and monobodies.

The term "diabodies" refers to small antibody fragments with two antigen-binding sites, which fragments comprise a heavy-chain variable domain (VH) connected to a light-chain variable domain (VL) in the same polypeptide chain (VH-VL). Preferably, by using a linker that is too short to allow pairing between the two domains on the same chain, the domains are forced to pair with the complementary domains of another chain and create two antigen-binding sites.

The term "monobodies" as used herein, refers to antigen binding molecules with a heavy chain variable domain and no light chain variable domain. A monobody can bind to an antigen in the absence of light chain and typically has three CDR regions designated CDRH1, CDRH2 and CDRH3. Monobodies include "camelid monobodies" such as VHH fragments obtained from a source animal of the camelid family, including animals with feet with two toes and leathery soles. Animals in the camelid family include camels, llamas, and alpacas. It has been reported that camels (Camelus dromedaries and Camelus bactrianus) often lack variable light chain domains when material from their serum is analysed, suggesting that sufficient antibody specificity and affinity can be derived from VH domains (three CDR loops) alone. Monobodies also include modified VH from various animal sources, in particular mammals (for example mouse, rat, rabbit, horse, donkey, bovine or human), which can bind to an antigen in the absence of VL. Preferably, the VH is modified in positions at the VL interface to provide for binding of the VH to antigen in absence of the VL. One skilled in the art is able to optimize a human VH by substitution of some important residues (by "camelization") to mimic camelid antibody heavy chains naturally devoid of light chain partners. This permits to obtain antibody functional fragments with stability properties and expression levels similar to camelid VHH while keeping the recognition properties of the antibody fragment, including high affinity and high specificity and decreasing immunogenicity.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(_{ab}')_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

In one particular embodiment, the invention relates to a functional fragment of an antibody of the invention wherein said fragment is chosen among the group comprising or consisting of Fab, Fab', F(ab')$_2$, Facb, Fd, scFv, diabodies and monobodies including VHH fragments and human VH fragments.

According to the invention, said functional fragment are capable of recognizing the O-acetylated-GD2 ganglioside.

Preferably a functional fragment of the antibody of the invention retains an equivalent activity, particularly an equivalent cytotoxic activity, to that of an antibody of the invention.

The expression "recognizing the O-acetylated-GD2 ganglioside" means that the antibody of the invention is able to bind the O-acetylated-GD2 ganglioside with an affinity of less than $10^{-7}$ M, preferably less than $5 \times 10^{-8}$ M and more preferably less than $10^{-8}$ M.

Preferably, but not necessarily, the antibodies useful in the invention are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is well-known.

As it is well understood in the art, monoclonal antibodies can readily be generated with appropriate specificity by standard techniques of immunization of mammals forming produces it. These nucleotide sequences can then be manipulated to provide them in humanized form.

By "chimeric antibody" is meant an antibody that is composed of variable regions from a murine immunoglobulin and of constant regions of a human immunoglobulin. This alteration consists simply of substituting the constant region of a human antibody for the murine constant region, thus resulting in a human/murine chimera which may have sufficiently low immunogenicity to be acceptable for pharmaceutical use.

A number of methods for producing such chimeric antibodies have yet been reported, thus forming part of the general knowledge of the skilled artisan (See, e.g., U.S. Pat. No. 5,225,539).

By "humanized antibody" is meant an antibody that is composed partially or fully of amino acid sequences derived from a human antibody germline by altering the sequence of an antibody having non-human complementarity determining regions (CDR). This humanization of the variable region of the antibody and eventually the CDR is made by techniques that are by now well known in the art.

As an example, British Patent Application GB 2188638A and U.S. Pat. No. 5,585,089 disclose processes wherein recombinant antibodies are produced where the only portion of the antibody that is substituted is the complementarity determining region, or "CDR". The CDR grafting technique has been used to generate antibodies which consist of murine CDRs, and human variable region framework and constant regions (See. e. g., RIECHMANN et al., Nature, vol. 332, p: 323-327, 1988). These antibodies retain the human constant regions that are necessary for Fc dependent effector function, but are much less likely to evoke an immune response against the antibody.

As an example, the framework regions of the variable regions are substituted by the corresponding human framework regions leaving the non-human CDR substantially intact, or even replacing the CDR with sequences derived from a human genome (See e.g. Patent application US 2006/0258852). Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i.e., at least about 85 or 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

Humanized antibodies have at least three potential advantages over non-human and chimeric antibodies for use in human therapy:
1) Because the effector portion is human, it may interact better with the other parts of the human immune system (e.g., destroy the target cells more efficiently by complement-dependent cytotoxicity (CDC) or antibody-dependent cellular cytotoxicity (ADCC)).
2) The human immune system should not recognize the framework or C region of the humanized antibody as foreign, and therefore the antibody response against such an injected antibody should be less than against a totally foreign non-human antibody or a partially foreign chimeric antibody.
3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

As an example, the design of humanized immunoglobulins may be carried out as follows: When an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 Å (center-to-center) of any atom of a CDR amino acid in a three dimensional immunoglobulin model (QUEEN et al., Proc. Natl. Acad. Sci. USA, vol. 88, p: 2869, 1991). When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

In a particular embodiment, the antibody of the invention is a chimeric antibody.

In a preferred embodiment, said antibody is a chimeric antibody and the light and heavy chain framework sequences are from mouse immunoglobulin light and heavy chains respectively.

Preferably, said chimeric antibody further comprises the constant regions from human light and heavy chains.

According to the invention, a chimeric antibody of the invention is capable of recognizing the O-acetylated-GD2 ganglioside.

Preferably, a chimeric antibody of the invention retains an equivalent activity, particularly an equivalent cytotoxic activity, to that of an antibody of the invention.

Advantageously, said antibody comprises a light chain variable region (LCVR) comprising the amino acid sequence SEQ ID NO:9.

Again advantageously, said antibody comprises a heavy chain variable region (HCVR) comprising the amino acid sequence SEQ ID NO:10.

In a more preferred embodiment, said antibody comprises a light chain variable region comprising the amino acid sequence SEQ ID NO:9 and a heavy chain variable region (HCVR) comprising the amino acid sequence SEQ ID NO:10.

```
SEQ ID NO: 9    DVVMTQTPLS LPVSLGDQAS ISCRSSQSLL KNNGNTFLHW
                YLQKSGQSPK LLIYKVSNRL SGVPDRFSGS GSGTYFTLKI
                SRVEAEDLGV YFCSQSTHIP YTFGGGTKLE IK

SEQ ID NO: 10   EVKLVESGGG LVLPGDSLRL SCATSEFTFT DYYMTWVRQP
                PRKALEWLGF IRNRANGYTT EYNPSVKGRF TISRDNSQSI
                LYLQMNTLRT EDSATYYCAR VSNWAFDYWG QGTTLTVSS
```

In another particular embodiment, the antibody of the invention is a humanized antibody.

In another preferred embodiment, said antibody is a humanized antibody and the light and heavy chain framework sequences are from humanized immunoglobulin light and heavy chains respectively.

Preferably, a humanized antibody of the invention further comprises the constant regions from human light and heavy chains.

According to the invention, a humanized antibody of the invention is capable of recognizing the O-acetylated-GD2 ganglioside.

Preferably, a humanized antibody of the invention retains an equivalent activity, particularly an equivalent cytotoxic activity, to that of an antibody of the invention.

Other sequences are possible for the light and heavy chains for the humanized antibodies of the present invention. The immunoglobulins can have two pairs of light chain/heavy chain complexes, at least one chain comprising one or more mouse complementarity determining regions functionally joined to human framework region segments.

The antibodies of the invention encompass immunoconjugates.

As used herein, the term "immunoconjugate" refers to a conjugate molecule comprising at least one antibody or a functional fragment thereof, bound to a second molecule, preferably a cytotoxic agent or a radioisotope. Preferably, said antibody or functional fragment thereof is bound to said second molecule by covalent linkage.

In one embodiment, the antibody of the invention is an immunoconjugate.

In a particular embodiment, the antibody of the invention is an immunoconjugate wherein said immunoconjugate comprises an antibody of the invention or a functional fragment thereof and a cytotoxic agent.

In another particular embodiment, the antibody of the invention is an immunoconjugate wherein said immunoconjugate comprises an antibody of the invention or a functional fragment thereof and a radioisotope.

The term "Cancer Stem Cells cancer" or "CSC cancer" refers to a cancer comprising particular cells known as cancer stem cells.

In one embodiment, a CSC cancer comprises at least 0.1% of cancer stem cells; preferably a CSC cancer comprises 1% to 95% of cancer stem cells, most preferably a CSC cancer comprises 1% to 50% of cancer stem cells.

The term "cancer stem cells" has its general meaning in the art and refers to a subpopulation of cancer cells (found within solid tumors and haematological cancers) that possess characteristics associated with normal stem cells, specifically the ability to give rise to all cell types found in a particular cancer sample. They have the capacity for self-renewal, differentiation into multiple cancer cell lineages and extensive proliferation. They can initiate new tumor with only a small amount of cancer stem cells and tend to be resistant to conventional therapy including chemotherapy and radiotherapy.

Thus, by targeting CSC, the anti-OAcGD2 antibody enables to prevent and/or to treat metastasis resulting from these CSC.

These cancer stem cells can be isolated from tumors by surface markers, such as CD133, CD44, CD34, CD24, ALDH1; these markers permit to distinguish cancer stem cells among the bulk of cancer cells. These cell surface markers can be recognized by reagents that specifically bind to the cell surface markers. For example, proteins, carbohydrates, or lipids on the surface of cancer stem cells can be immunologically recognized by antibodies specific for the particular protein or carbohydrate. The set of markers present on the cell surface of cancer stem cells and absent from the cell surface of these cells is characteristic for cancer stem cells. Therefore, cancer stem cells can be selected by positive and negative selection of cell surface markers. A reagent that binds to a cancer stem cell is a "positive marker" (i.e. a marker that is present on the cell surface of cancer stem cells). A reagent that does not bind to a cancer stem cell is a "negative marker" (i.e. a marker that is not present on the cell surface of cancer stem cells).

The discrimination between cells based upon the detected expression of cell surface markers is by comparing the detected expression of cell surface marker as compared with the mean expression by a control population of cells. For example, the expression of a marker on a cancer stem cell can be compared to the mean expression of the marker by the other cell derived from the same tumor as the cancer stem cell. Other methods of discriminating among cells by marker expression include method of gating cells by flow cytometry based upon marker expression.

While it is rare to identify a single marker that identifies a cancer stem cell, it has often been possible to identify combinations of positive and negative markers that uniquely identify cancer stem cells. Combinations of markers, either positive and/or negative, allow obtaining specific phenotype for cancer stem cells depending on cancer type. Several methods are currently known in the art to specifically isolate cancer stem cells in vitro, including the widely used approaches specific markers or Hoechst staining-based isolation, but also the chemoresistance based isolation, heterogeneity of invasiveness sorting and, in metastatic breast cancer cells, reoxygenation sorting after exposure to repetitive cycles of hypoxia.

Cancer stem cells have been identified in very different types of cancers, including, but not limited to, leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer.

Thus, in one embodiment of the invention, the CSC cancer of the invention is chosen among the group comprising or consisting of leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer.

In a preferred embodiment, said CSC cancer is glioma, breast cancer, acute lymphoid leukemia or acute myeloid leukemia.

Different markers have been observed as identifying cancer stem cells among the bulk of cancer cells, such markers varying and depending on the type of cancer.

Examples of markers that can be used to identify CSC cancer comprise, but are not limited to, CD34, CD38, CD19, interleukin-3-receptor α (CD123), CD33, CD44, CD44v6, CD47, CD24, EpCAM (ESA), Lin, CD133, A2B5, SSEA-1, CD166, CD26, CD200, α2β1, Sca, CD45, Pecam, ALDH, ALDH1, Oct4, ABCG2, CXCR4, AFP, EMA, IGF-IR, and Nestin.

However, it has to be noted that the known cancer stem cells markers may be used to identify CSC cancer, but are not suitable as target antigen to treat said cancer, as they are mostly expressed on healthy tissues.

Some examples of cancer stem cells phenotypes comprise the phenotypes described in Table 1:

TABLE 1

Biomarkers and/or phenotypes of different cancer stem cells.

| Cancer type | CSC biomarkers and/or phenotypes |
| --- | --- |
| Acute myeloid leukemia | CD34$^+$/CD38$^-$ |
| | interleukin-3-receptor α$^+$ |
| | CD33$^+$ |
| Acute lymphoid leukemia | CD34$^+$/CD19$^+$ |
| | CD34$^+$/CD19$^-$ |
| | CD34$^+$/CD38$^+$/CD19$^+$ |
| | CD34$^+$/CD38$^-$/CD19$^+$ |
| | interleukin-3-receptor α$^+$ |
| | CD33$^+$ |
| | CD133$^+$/CD38$^-$ |
| | CD133$^+$/CD19$^-$ |
| Breast cancer | CD44$^+$/CD24$^{-/low}$ |
| | CD44$^+$/CD24$^{-/low}$/ESA$^+$ |
| | CD44$^+$/CD24$^{-/low}$/lin$^-$/ALDH1$^+$ |
| Glioma cancer | CD133$^+$ |
| | A2B5$^+$ |
| | SSEA-1$^+$ |
| Colorectal cancer | CD133$^+$/ESA$^{high}$/CD44$^+$ |
| | CD166$^+$ |
| | CD26$^+$ |
| Pancreatic cancer | CD133$^+$ |
| | CD44$^+$/CD24$^+$/ESA$^+$ |
| Prostate cancer | CD44$^+$/CD133$^+$/α2β1$^+$ |
| | CD44$^+$ |
| Lung cancer | Sca$^+$/CD45$^-$/Pecam$^-$/CD34$^+$ |
| | ALDH1$^+$/Oct4$^+$/CD133$^+$/ABCG2$^+$/CXCR4$^+$ |
| Liver cancer | CD133$^+$/CD44$^+$ |
| | EpCAM$^+$/AFP$^+$ |
| Bladder cancer s | EMA$^-$/CD44v6$^+$ |
| Gastric cancer | CD133$^+$/CD44$^+$ |
| | CD44$^+$, CD133$^+$/CD44$^+$/ALDH1$^+$ |

Thus, in one embodiment, said CSC cancer comprises cells having at least one phenotype chosen among the group comprising or consisting of: CD34$^+$/CD38$^-$, CD34$^+$/CD19$^-$, CD34$^+$/CD19$^+$, CD34$^+$/CD38$^+$/CD19$^+$, CD34$^+$/CD38$^-$/CD19$^+$, CD133$^+$/CD38$^-$, CD133$^+$/CD19$^-$, interleukin-3-receptor α$^+$, CD33$^+$, CD44$^+$/CD24$^{-/low}$, CD44$^+$/CD24$^-$/ESA$^+$, CD44$^+$/CD24$^{-/low}$/lin$^-$/ALDH1$^+$, CD133$^+$, A2B5$^+$, SSEA-1$^+$, CD133$^+$/ESA$^{high}$/CD44$^+$, CD166$^+$, CD26$^+$, CD44$^+$/CD133$^+$/α2β1$^+$, CD44$^+$, Sca$^+$/CD45$^-$/Pecam$^-$/CD34$^+$, ALDH1$^+$/Oct4$^+$/CD133$^+$/ABCG2$^+$/CXCR4$^+$, CD133$^+$/CD44$^+$, EpCAM$^+$/AFP$^+$, EMA$^-$/CD44v6$^+$, CD133$^+$/CD44$^+$/ALDH1$^+$.

In one embodiment of the invention, the CSC cancer of the invention comprises CD133$^+$ cells.

In another embodiment, the CSC cancer of the invention comprises CD44$^+$ cells. In a more particular embodiment, the CSC cancer of the invention comprises CD44$^+$/CD24$^{-/low}$ cells.

In still another embodiment, the CSC cancer of the invention comprises CD34$^+$.

In a more particular embodiment, the CSC cancer of the invention comprises CD34$^+$/CD38$^-$ cells.

In another more particular embodiment, the CSC cancer of the invention comprises CD34$^+$/CD19$^+$ cells, preferably CD34$^+$/CD38$^+$/CD19$^+$ or CD34$^+$/CD38$^-$/CD19$^+$ cells.

In a preferred embodiment of the invention, a CSC cancer of the invention is characterized by a subpopulation of cancer stem cells in which at least 10% of cancer stem cells presenting the O-acetylated-GD2 ganglioside at their surface, preferably at least 30% of cancer stem cells, and most preferably at least 50% of cancer stem cells presenting the O-acetylated-GD2 ganglioside at their surface.

In a particular embodiment of the invention, said CSC cancer is breast cancer.

In a more particular embodiment, said CSC cancer is breast cancer wherein cancer stem cells are characterized by a CD44$^+$/CD24$^{-/low}$ phenotype.

In another particular embodiment of the invention, said CSC cancer is glioma.

In a more particular embodiment, said CSC cancer is glioma wherein cancer stem cells are characterized by a CD133$^+$ phenotype.

In another particular embodiment of the invention, said CSC cancer is leukemia, more particularly acute myeloid leukemia or acute lymphoid leukemia.

In a more particular embodiment, said CSC cancer is leukemia wherein cancer stem cells are characterized by a CD34$^+$ phenotype, more particularly said CSC cancer is acute myeloid leukemia wherein cancer stem cells are characterized by a CD34$^+$/CD38$^-$ phenotype or acute lymphoid leukemia wherein cancer stem cells are characterized by a CD34$^+$/CD19$^+$ phenotype, preferably a CD34$^+$/CD19$^+$/CD38$^-$ or CD34$^+$/CD19$^+$/CD38$^+$ phenotype.

In the context of the invention, the term "treating CSC cancer" means reversing, alleviating, inhibiting the progress or propagation of CSC cancer and/or metastasis. The term also encompasses preventing CSC cancer, metastasis or CSC cancer recurrence. Preferably such treatment also leads to the regression of tumor growth, i.e., the decrease in size of a measurable tumor. Typically, such treatment leads to a prolongation of patient survival without CSC cancer progression, recurrence or to a prolongation of its overall survival.

In one embodiment, the invention relates to an antibody of the invention for treating metastasis or metastases of a CSC cancer.

In the context of the invention, the term "treating metastasis" encompasses preventing metastasis of a CSC cancer.

In another embodiment, the invention relates to an antibody of the invention for preventing relapse or recurrence of a CSC cancer.

The antibody of the invention for the treatment of CSC cancer is used to improve the survival (more particularly the 5-year survival rate) of patients afflicted with a CSC cancer.

Thus, in one particular embodiment, the invention relates to an antibody of the invention for the treatment of a CSC cancer, said CSC cancer being a cancer associated with a bad prognosis.

As used herein, a cancer associated with a bad prognosis corresponds to cancer a cancer associated to a median prognosis of less than 5 years, preferably less than 2 years and still preferably less than 1 year.

In this context, the antibody of the invention is preferably used in combination with at least one other anti-cancer compound or one other anti-cancer therapy for the treatment of CSC cancer. This combination may potentiate the effects of the anti-cancer therapy and decrease the risk of propagation, relapse or recurrence of said CSC cancer.

Anti-cancer compounds and therapies are various and well known in the art. They encompass conventional and generalist anti-cancer strategies such as chemotherapy, radiotherapy, surgery but also hormonal therapy. They also comprise more specific therapies including targeted therapy, including monoclonal antibodies directed against tumor antigens and tyrosine kinase and CDK inhibitors, angiogenesis inhibitors . . . .

In one embodiment, the invention relates to an antibody of the invention and at least one other anti-cancer compound as a combined preparation for separate, simultaneous or sequential use in the treatment of CSC cancer.

In another embodiment, the invention relates to an antibody of the invention combined with surgery, chemotherapy, hormonal therapy, targeted therapy and/or radiotherapy for separate, simultaneous or sequential use in the treatment of CSC cancer.

Combination of an antibody of the invention with another cancer treatment could lead to complete regression of the tumor.

A second object of the invention relates to a pharmaceutical composition for treating CSC cancer, said pharmaceutical composition comprising an antibody of the invention or a functional fragment thereof.

Antibodies of the invention are described above.

According to the invention, said antibody comprises:
a) A light chain comprising at least a light chain variable region framework from an immunoglobulin and three complementary determining regions (CDRs) defined by the sequences SEQ ID NO:1 for CDR-L1, SEQ ID NO:2 for CDR-L2, SEQ ID NO:3 for CDR-L3, and/or
b) An heavy chain comprising at least a heavy chain variable region framework from an immunoglobulin and three complementary determining regions (CDRs) defined by the sequences SEQ ID NO:4 for CDR-H1, SEQ ID NO:5 for CDR-H2, SEQ ID NO:6 for CDR-H3.

In a particular embodiment, the antibody of the invention comprises:
a) A light chain comprising a light chain framework from an immunoglobulin light chain and three complementary determining regions (CDRs) defined by the sequences SEQ ID NO:1 for CDR-L1, SEQ ID NO:2 for CDR-L2, SEQ ID NO:3 for CDR-L3, and/or
b) An heavy chain comprising a heavy chain framework from an immunoglobulin heavy chain and three complementary determining regions (CDRs) defined by the sequences SEQ ID NO:4 for CDR-H1, SEQ ID NO:5 for CDR-H2, SEQ ID NO:6 for CDR-H3.

In another embodiment, said composition comprises a functional fragment of an antibody of the invention wherein said fragment is chosen among the group comprising or consisting of Fab, Fab', F(ab')$_2$, Facb, Fd, scFv, diabodies and monobodies including VHH fragments and human VH fragments.

According to the invention, said fragment comprises the CDRs of the antibody of the invention and is capable of recognizing the O-acetylated-GD2 ganglioside.

In another embodiment, said composition comprises an antibody of the invention wherein said antibody is a chimeric antibody.

In a preferred embodiment, said antibody comprises a light chain variable region comprising the amino acid sequence SEQ ID NO:7 and a heavy chain variable region comprising the amino acid sequence SEQ ID NO:8.

In another embodiment, said composition comprises an antibody of the invention wherein said antibody is a humanized antibody.

In another embodiment, the antibody of the invention is an immunoconjugate.

In a particular embodiment, the antibody of the invention is an immunoconjugate wherein said immunoconjugate comprises an antibody of the invention or a functional fragment thereof and a cytotoxic agent.

In another particular embodiment, the antibody of the invention is an immunoconjugate wherein said immunoconjugate comprises an antibody of the invention or a functional fragment thereof and a radioisotope.

CSC cancers of the invention are also described above.

In one embodiment, the composition of the invention is for treating a CSC cancer chosen among the group comprising or consisting of leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer.

In a preferred embodiment, said CSC cancer is glioma, breast cancer, acute lymphoid leukemia or acute myeloid leukemia.

In another embodiment, said CSC cancer comprises cells having at least one phenotype chosen among the group comprising or consisting of: $CD34^+/CD38^-$, $CD34^+/CD19^-$, $CD34^+/CD19^+$, $CD34^+/CD38^+/CD19^+$, $CD34^+/CD38^-/CD19^+$, $CD133^+/CD38^-$, $CD133^+/CD19^-$, interleukin-3-receptor $\alpha^+$, $CD33^+$, $CD44^+/CD24^{-/low}$, $CD44^+/CD24^-/ESA^+$, $CD44^+/CD24^{-/low}/lin^-/ALDH1^+$, $CD133^+$, $A2B5^+$, $SSEA-1^+$, $CD133^+/ESA^{high}/CD44^+$, $CD166^+$, $CD26^+$, $CD44^+/CD133^+/\alpha2\beta1^+$, $CD44^+$, $Sca^+/CD45^-/Pecam^-/CD34^+$, $ALDH1^+/Oct4^+/CD133^+/ABCG2^+/CXCR4^+$, $CD133^+/CD44^+$, $EpCAM^+/AFP^+$, $EMA^-/CD44v6^+$, $CD133^+/CD44^+/ALDH1^+$.

In a more particular embodiment of the invention, the CSC cancer of the invention comprises $CD133^+$ cells, $CD44^+$ cells, more particularly $CD44^+/CD24^{-/low}$ cells, or $CD34^+$ cells, more particularly $CD34^+/CD38^-$ or $CD34^+/CD19^+$ cells, even more particularly $CD34^+/CD19^+/CD38^-$ or $CD34^+/CD19^+/CD38^+$ cells.

In a preferred embodiment of the invention, the CSC cancer of the invention is characterized by a subpopulation of cancer stem cells in which at least 10% of cancer stem cells express the O-acetylated-GD2 ganglioside, preferably at least 30% of cancer stem cells, and most preferably at least 50% of stem cells express the O-acetylated-GD2 ganglioside.

In a particular embodiment of the invention, said CSC cancer is breast cancer. In a more particular embodiment, said CSC cancer is breast cancer wherein cancer stem cells are characterized by a $CD44^+/CD24^{-/low}$ phenotype.

In another particular embodiment of the invention, said CSC cancer is glioma. In a more particular embodiment, said CSC cancer is glioma wherein cancer stem cells are characterized by a $CD133^+$ phenotype.

In another particular embodiment of the invention, said CSC cancer is leukemia wherein cancer stem cells are characterized by a $CD34^+$ phenotype, more particularly said CSC cancer is acute myeloid leukemia wherein cancer stem cells are characterized by a $CD34^+/CD38^-$ phenotype or acute lymphoid leukemia wherein cancer stem cells are characterized by a $CD34^+/CD19^+$ phenotype, preferably a $CD34^+/CD19^+/CD38^-$ or $CD34^+/CD19^+/CD38^+$ phenotype.

In one embodiment, the invention relates to a composition of the invention for treating metastasis or metastases of a CSC cancer.

In another embodiment, the invention relates to a composition of the invention for preventing relapse or recurrence of a CSC cancer.

Thus, in one particular embodiment, the invention relates to a composition of the invention for the treatment of a CSC cancer, wherein said CSC cancer is a cancer associated with a bad prognosis.

In one embodiment, the invention relates to a composition of the invention and at least one other anti-cancer compound as a combined preparation for separate, simultaneous or sequential use in the treatment of CSC cancer.

In another embodiment, the invention relates to a composition of the invention combined with surgery, chemotherapy, hormonal therapy, targeted therapy and/or radiotherapy for separate, simultaneous or sequential use in the treatment of CSC cancer.

The pharmaceutical composition of the invention further comprises a pharmaceutically acceptable carrier.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or State government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

The route of administration of the composition of the invention is preferably parenteral; as used herein, the term "parenteral" includes intratumoral, intravenous, intramuscular, subcutaneous, rectal, vaginal or intraperitoneal administration. Thus, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin. Of these, intravenous or intratumoral administration is most preferred.

The antibody may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly (lactide-co-glycolic acid) (PLGA)); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Dispersions can also be prepared in glycerol, liquid polyethylene glycols, mixtures thereof and in oils. Under ordinary conditions of storage and use, these preparations contain a preservative to prevent the growth of microorganisms.

The antibody can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetable oils. The conjugates of the invention may also be modified, by pegylation as an example, so as to increase its biodisponibility.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, half-life enhancing covalent and non-covalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (e.g. glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In one embodiment of the invention, the pharmaceutical composition of the invention further comprises an additional active compound in separate or unit dosage form for separate, simultaneous or sequential use or administration.

A third object of the invention relates to a method for treating a CSC cancer in a subject comprising administering to said subject in need thereof an effective amount of an antibody or a composition of the invention.

As used herein, the term "subject" refers to a mammal, such as a rodent, a feline, a canine or a primate, and most preferably a human.

Compositions and antibodies of the invention are described in detailed above.

In one embodiment, the invention relates to said method for treating a CSC cancer chosen among the group comprising or consisting of leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer.

In a preferred embodiment, said CSC cancer is glioma, breast cancer, acute lymphoid leukemia or acute myeloid leukemia.

In another embodiment, said CSC cancer comprises cells having at least one phenotype chosen among the group comprising or consisting of: $CD34^+/CD38^-$, $CD34^+/CD19^-$, $CD34^+/CD19^+$, $CD34^+/CD38^+/CD19^+$, $CD34^+/CD38^-/CD19^+$, $CD133^+/CD38^-$, $CD133^+/CD19^-$, interleukin-3-receptor $\alpha^+$, $CD33^+$, $CD44^+/CD24^{-/low}$, $CD44^+/CD24^-/ESA^+$, $CD44^+/CD24^{-/low}/lin^-/ALDH1^+$, $CD133^+$, $A2B5^+$, $SSEA-1^+$, $CD133^+/ESA^{high}/CD44^+$, $CD166^+$, $CD26^+$, $CD44^+/CD133^+/\alpha2\beta1^+$, $CD44^+$, $Sca^+/CD45^-/Pecam^-/CD34^+$, $ALDH1^+/Oct4^+/CD133^+/ABCG2^+/CXCR4^+$, $CD133^+/CD44^+$, $EpCAM^+/AFP^+$, $EMA^-/CD44v6^+$, $CD133^+/CD44^+/ALDH1^+$.

In a more particular embodiment of the invention, the CSC cancer of the invention comprises $CD133^+$ cells, $CD44^+$ cells, more particularly $CD44^+/CD24^{-/low}$ cells, or $CD34^+$ cells, more particularly $CD34^+/CD38^-$ or $CD34^+/CD19^+$ cells, even more particularly $CD34^+/CD19^+/CD38^-$ or $CD34^+/CD19^+/CD38^+$ cells.

In a preferred embodiment of the invention, the CSC cancer of the invention is characterized by a subpopulation of cancer stem cells in which at least 10% of cancer stem cells presenting the O-acetylated-GD2 ganglioside at their surface, preferably at least 30% of cancer stem cells, and most preferably at least 50% of stem cells presenting the O-acetylated-GD2 ganglioside at their surface.

In a particular embodiment of the invention, said CSC cancer is breast cancer. In a more particular embodiment, said CSC cancer is breast cancer wherein cancer stem cells are characterized by a $CD44^+/CD24^{-/low}$ phenotype.

In another particular embodiment of the invention, said CSC cancer is glioma. In a more particular embodiment, said CSC cancer is glioma wherein cancer stem cells are characterized by a $CD133^+$ phenotype.

In another particular embodiment of the invention, said CSC cancer is leukemia wherein cancer stem cells are characterized by a $CD34^+$ phenotype, more particularly said CSC cancer is acute myeloid leukemia wherein cancer stem cells are characterized by a $CD34^+/CD38^-$ phenotype or acute lymphoid leukemia wherein cancer stem cells are characterized by a $CD34^+/CD19^+$ phenotype, preferably a $CD34^+/CD19^+/CD38^-$ or $CD34^+/CD19^+/CD38^+$ phenotype.

In one embodiment, the invention relates to said method for treating metastasis or metastases of a CSC cancer.

In another embodiment, the invention relates to said method for preventing relapse or recurrence of a CSC cancer.

In a particular embodiment, the invention relates to a method for treating a CSC cancer of the invention, wherein said CSC cancer is a cancer associated with a bad prognosis.

In one embodiment, the invention relates to a method for treating a CSC cancer in a subject comprising administering to said subject in need thereof an effective amount of an antibody or a composition of the invention and at least one other anti-cancer compound as a combined preparation for separate, simultaneous or sequential use in the treatment of CSC cancer.

In another embodiment, the invention relates to a method for treating CSC cancer of the invention combined with surgery, chemotherapy, hormonal therapy, targeted therapy and/or radiotherapy for separate, simultaneous or sequential use in the treatment of CSC cancer.

An "effective amount" of the composition is an amount which is sufficient to induce the regression of tumor growth. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

As an illustration, an effective amount of the at least one conjugate is from about 50 to about 1,000 $mg/m^2$, more preferably from about 100 to about 750 $mg/m^2$, and most preferably from about 250 to about 500 $mg/m^2$. Other dosages are viable, since the molecular weight of the conjugate thereof may influence it. The skilled artisan is readily credited with determining a suitable dosage that falls within the ranges, or if necessary, outside of the ranges.

Diagnostic Strategies of the Invention

A fourth object of the invention relates to a method for diagnosing a CSC cancer in a subject, wherein said method comprises determining the expression of the O-acetylated-GD2 ganglioside, and wherein an expression of the O-acetylated-GD2 ganglioside is indicative of a CSC cancer.

In one embodiment, the present invention relates to method of detecting O-acetylated-GD2 ganglioside (OAcGD2) in a subject suspected of having a cancer stem cell (CSC) cancer, comprising:
  i) Obtaining a biological sample comprising tumor cells from said subject;
  ii) Detecting whether OAcGD2 is coexpressed with at least one CSC biomarker selected from the group consisting of:

| Cancer type | CSC biomarkers and/or phenotypes |
| --- | --- |
| Acute myeloid leukemia | $CD34^+/CD38^-$ |
| | interleukin-3-receptor $\alpha^+$ |
| | $CD33^+$ |
| Acute lymphoid leukemia | $CD34^+/CD19^+$ |
| | $CD34^+/CD19^-$ |
| | $CD34^+/CD38^+/CD19^+$ |
| | $CD34^+/CD38^-/CD19^+$ |
| | interleukin-3-receptor $\alpha^+$ |
| | $CD33^+$ |
| | $CD133^+/CD38^-$ |
| | $CD133^+/CD19^-$ |
| Breast cancer | $CD44^+/CD24^{-/low}$ |
| | $CD44^+/CD24^{-/low}/ESA^+$ |
| | $CD44^+/CD24^{-/low}/lin^-/ALDH1^+$ |
| Glioma cancer | $CD133^+$ |
| | $A2B5^+$ |
| | $SSEA-1^+$ |
| Colorectal cancer | $CD133^+/ESA^{high}/CD44^+$ |
| | $CD166^+$ |
| | $CD26^+$ |
| Pancreatic cancer | $CD133^+$ |
| | $CD44^+/CD24^+/ESA^+$ |
| Prostate cancer | $CD44^+/CD133^+/\alpha2\beta1^+$ |
| | $CD44^+$ |
| Lung cancer | $Sca^+/CD45^-/Pecam^-/CD34^+$ |
| | $ALDH1^+/Oct4^+/CD133^+/ABCG2^+/CXCR4^+$ |
| Liver cancer | $CD133^+/CD44^+$ |
| | $EpCAM^+/AFP^+$ |

| Cancer type | CSC biomarkers and/or phenotypes |
| --- | --- |
| Bladder cancer s | EMA$^-$/CD44v6$^+$ |
| Gastric cancer | CD133$^+$/CD44$^+$ |
| | CD44$^+$, CD133$^+$/CD44$^+$/ALDH1$^+$ | at the surface of CSC by contacting the biological sample with an anti-OAcGD2 antibody and with at least one antibody specific for the at least one CSC biomarker and detecting binding between OAcGD2 and the corresponding antibody and between the at least one CSC biomarker and the corresponding antibody.

In a particular embodiment, the anti-OAcGD2 antibody comprises a heavy chain variable region comprising SEQ ID NO:7 and a light chain variable region comprising SEQ ID NO:8.

The applicants have now demonstrated, surprisingly, that the use of the tumor marker OacGD2, in combination with the CSC markers recited in table 1, which are present on cell surface of cancer stem cells, such that they can be detected both in biological samples remote from the tumors and in the tumors themselves, makes it possible to substantially improve the diagnosis of cancer stem cell cancers.

Surprisingly, the presence or the absence at the cell surface of cancer stem cells, of one given marker is not systematically observed in the same patients. As a result, the combination of several tumor markers makes it possible to increase the number of patients identified as having cancer stem cell cancer.

By identifying a new surface marker of cancer stem cells it is possible to more effectively diagnose the presence of malignant cells;

By identifying a new gene and protein expressed by cancer stem cells it is possible to identify protein which represent novel drug target; and By isolating cancer stems cells from individual patient and transplanting them into in vitro and in vivo functional assays it is possible to test the effectiveness of different drug regimens against them. This it is possible to predict drug sensitivity and drug resistance.

In one embodiment, the invention relates to method of diagnosing a cancer stem cell cancer comprising cells having at least one phenotype selected from the group selected from the group consisting of:

| Cancer type | CSC biomarkers and/or phenotypes |
| --- | --- |
| Acute myeloid leukemia | CD34$^+$/CD38$^-$ |
| | interleukin-3-receptor α$^+$ |
| | CD33$^+$ |
| Acute lymphoid leukemia | CD34$^+$/CD19$^+$ |
| | CD34$^+$/CD19$^-$ |
| | CD34$^+$/CD38$^+$/CD19$^+$ |
| | CD34$^+$/CD38$^-$/CD19$^+$ |
| | interleukin-3-receptor α$^+$ |
| | CD33$^+$ |
| | CD133$^+$/CD38$^-$ |
| | CD133$^+$/CD19$^-$ |
| Breast cancer | CD44$^+$/CD24$^{-/low}$ |
| | CD44$^+$/CD24$^{-/low}$/ESA$^+$ |
| | CD44$^+$/CD24$^{-/low}$/lin$^-$/ALDH1$^+$ |
| Glioma cancer | CD133$^+$ |
| | A2B5$^+$ |
| | SSEA-1$^+$ |
| Colorectal cancer | CD133$^+$/ESA$^{high}$/CD44$^+$ |
| | CD166$^+$ |
| | CD26$^+$ |

| Cancer type | CSC biomarkers and/or phenotypes |
| --- | --- |
| Pancreatic cancer | CD133$^+$ |
| | CD44$^+$/CD24$^+$/ESA$^+$ |
| Prostate cancer | CD44$^+$/CD133$^+$/α2β1$^+$ |
| | CD44$^+$ |
| Lung cancer | Sca$^+$/CD45$^-$/Pecam$^-$/CD34$^+$ |
| | ALDH1$^+$/Oct4$^+$/CD133$^+$/ABCG2$^+$/CXCR4$^+$ |
| Liver cancer | CD133$^+$/CD44$^+$ |
| | EpCAM$^+$/AFP$^+$ |
| Bladder cancer s | EMA$^-$/CD44v6$^+$ |
| Gastric cancer | CD133$^+$/CD44$^+$ |
| | CD44$^+$, CD133$^+$/CD44$^+$/ALDH1$^+$ | in a subject, comprising:
i) Obtaining a biological sample comprising cancer stem cells from the subject;
ii) Detecting whether OAcGD2 is present on cancer stem cells by contacting the biological sample with an antibody that specifically binds to the O-acetylated-ganglioside (OAcGD2), wherein said anti-OAcGD2 antibody comprises a heavy chain variable region comprising SEQ ID NO:7 and a light chain variable region comprising SEQ ID NO:8, and detecting binding between OAcGD2 and the antibody that specifically binds to the OAcGD2;
iii) Diagnosing the subject with cancer stem cell cancer when the presence of the OAcGD2 on the cancer stem cells is detected; and
iv) Optionally, administering a therapeutic effective amount of the antibody that specifically binds to the OAcGD2 to the subject diagnosed as having cancer stem cell cancer.

In a preferred embodiment, the CSC cancer of the invention is characterized by a subpopulation of cancer stem cells in which at least 10% of cancer stem cells (CSC) express the O-acetylated-GD2 ganglioside, preferably at least 30% and most preferably at least 50% of CSC express the O-acetylated-GD2 ganglioside.

The use of combination of antibodies specific for cancer stem cell surface markers results in the method of the invention being useful for the detection and/or the identification of cancer stem cells from a variety of cancer stem cell cancer including acute myeloid leukemia, acute lymphoid leukemia, breast cancer, glioma cancer, pancreatic cancer, prostate cancer, lung cancer, liver cancer, bladder cancer and gastric cancer.

In one embodiment, the CSC diagnosed by the method of the invention have at least one phenotype selected from the group comprising or consisting of: OAcGD2$^+$/CD34$^+$/CD38$^-$, OAcGD2$^+$/CD34$^+$/CD19$^-$, OAcGD2$^+$/CD34$^+$/CD19$^+$, OAcGD2$^+$/CD34$^+$/CD38$^+$/CD19$^+$, OAcGD2$^+$/CD34$^+$/CD38$^-$/CD19$^+$, OAcGD2$^+$/CD133$^+$/CD38$^-$, OAcGD2$^+$/CD133$^+$/CD19$^-$, OAcGD2$^+$/interleukin-3-receptor α$^+$, OAcGD2$^+$/CD33$^+$, OAcGD2$^+$/CD44$^+$/CD24$^{-/low}$, OAcGD2$^+$/CD44$^+$/CD24$^{-/low}$/ESA$^+$, OAcGD2$^+$/CD44$^+$/CD24$^{-/low}$/lin$^-$/ALDH1$^+$, OAcGD2$^+$/CD133$^+$, OAcGD2$^+$/A2B5$^+$, OAcGD2$^+$/SSEA-1$^+$, OAcGD2$^+$/CD133$^+$/ESA$^{high}$/CD44$^+$, OAcGD2$^+$/CD166$^+$, OAcGD2$^+$/CD26$^+$, OAcGD2$^+$/CD44$^+$/CD133$^+$/α2β1$^+$, OAcGD2$^+$/CD44$^+$, OAcGD2$^+$/Sca$^+$/CD45$^-$/Pecam$^-$/CD34$^+$, OAcGD2$^+$/ALDH1$^+$/Oct4$^+$/CD133$^+$/ABCG2$^+$/CXCR4$^+$, OAcGD2$^+$/CD133$^+$/CD44$^+$, OAcGD2$^+$/EpCAM$^+$/AFP$^+$, OAcGD2$^+$/EMA$^-$/CD44v6$^+$, OAcGD2$^+$/CD133$^+$/CD44$^+$/ALDH1$^+$.

In a particular embodiment, the CSC diagnosed by the method of the invention have the phenotype OAcGD2$^+$/

CD44$^+$/CD24$^{-/low}$, OAcGD2$^+$/CD44$^+$/CD24$^{-/low}$/ESA$^+$, or OAcGD2$^+$/CD44$^+$/CD24$^{-/low}$/lin$^-$/ALDH1$^+$.

By selecting for phenotypic characteristics among the cells obtained from a tumor, cancer stem cells can be isolated from any animal tumor, particularly any mammalian tumor. It will be appreciated that, taking into consideration factors such as a binding affinity, that antibodies that recognize species-specific varieties of markers are used to detect and/or to identify cancer stem cells. In one embodiment, the anti-OAcGD2 antibody binds the O-acetylated-GD2 ganglioside with an affinity of less than $10^{-7}$ M, preferably less than $5\times10^{-8}$ M and more preferably less than $10^{-8}$ M.

One of the major problems in identifying new cancer therapeutic agent is determining which of the myriad of genes identified in large scale microarray assays are the most clinically important drug targets. This is made especially difficult when studying cancer with solid tumors which consist of mixture of many types of normal cells and a heterogeneous population of tumor cells and cancer stem cells.

Instead, by the method of the invention, one can use flow cytometry and the xenograft model to enrich for specific cell populations. This has the advantage of being able to isolate cancer stem cells for molecular analysis. Thus, it is possible to test the functions of these cells and use them in biological assays, such as the production of growth factors, for tumorigenicity, drug resistance and metastatic potential.

The invention encompasses in vivo and in vitro methods.

In one embodiment, the invention relates to an in vitro method for diagnosing a CSC cancer in a subject, wherein said method comprises the step of analyzing a biological sample obtained from said subject by (i) determining the expression of the O-acetylated-GD2 ganglioside, and wherein an expression of the O-acetylated-GD2 ganglioside in said biological sample is indicative of a CSC cancer.

Advantageously, the determining step (i) is assessed by an antibody or functional fragment thereof as disclosed previously. Said antibody or fragment thereof may be labeled (e.g., a radio-labeled, chromophore-labeled, fluorophore-labeled, or enzyme-labeled antibody), or derived (e.g., an antibody conjugate with a substrate or with the protein or ligand of a protein of a protein/ligand pair (e.g., biotin-streptavidin)).

Said analysis can be assessed by a variety of techniques well known by one of skill in the art including, but not limited to, enzyme immunoassay (EIA), radioimmunoassay (RIA), Western blot analysis and enzyme linked immunoabsorbant assay (ELISA), Immuno Thin Layer Chromatography (ITLC), imaging techniques, particularly PET-Scan (Positron emission tomography) technique, flow cytometry or FACS.

The in vivo methods of the invention are assessed by an antibody the invention or a functional fragment thereof, which is suitable for an in vivo administration. Preferably, said in vivo methods are assessed by in vivo imaging methods, such as PET-Scan method. Such methods are well known in the art.

As used herein, the term "biological sample" means any biological sample derived from a patient, preferably said biological sample refers to a biopsy which has been removed from the body of a subject prior to executing the method of the invention. In one embodiment, the biological sample is obtained from a tumor, preferably a solid tumor or a blood sample.

In one embodiment, said CSC cancer is chosen among the group comprising or consisting of leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer.

In a preferred embodiment, said CSC cancer is a glioma, a breast cancer, an acute lymphoid leukemia or an acute myeloid leukemia.

A fifth object of the invention relates to the use of the O-acetylated-GD2 ganglioside as a biomarker of CSC cancer.

The term "O-acetylated-GD2 ganglioside" refers to a ganglioside derived from the GD2 ganglioside and corresponding to 9(7)-O-acetyl-GD2.

A sixth object of the invention relates to a method for predicting the response of a subject affected with CSC cancer to a treatment with an antibody or a composition of the invention, wherein said method comprises detecting the presence of cells expressing the O-acetylated-GD2 ganglioside in a biological sample of said subject.

In one embodiment, the invention relates to said method for predicting the response of a subject affected with CSC cancer to a treatment with an antibody or a composition of the invention, wherein the presence of cells expressing the O-acetylated-GD2 ganglioside in a biological sample of said subject correlates with a good probability that said subject ix responder to said treatment.

In a more particular embodiment, the invention relates to said method wherein said method comprises detecting the level of cancer stem cells expressing the O-acetylated-GD2 ganglioside among all cancer stem cells in a biological sample of said subject.

In a preferred embodiment, a level of at least 10%, particularly at least 30%, preferably at least 50% of cancer stem cells the O-acetylated-GD2 ganglioside at their surface among all cancer stem cells in a biological sample of said subject correlates with a high probability that said subject is a responder to said treatment.

In one embodiment, said biological sample is a cancer sample, preferably a CSC cancer sample.

In one embodiment, said CSC cancer is chosen among the group comprising or consisting of leukemia including acute myeloid leukemia and acute lymphoid leukemia, breast cancer, glioma including glioblastoma, colorectal cancer, pancreatic cancer, prostate cancer, lung cancer, liver cancer, bladder cancer or gastric cancer.

In a preferred embodiment, said CSC cancer is a glioma, a breast cancer, an acute lymphoid leukemia or an acute myeloid leukemia.

In one embodiment of the invention, said method comprises detecting the presence of cells expressing the O-acetylated-GD2 ganglioside within patients by non-invasive methods like imaging using an in vivo imaging agent. Such methods are well known in the art.

A seventh objet of the invention relates to a kit for diagnosing a cancer stem cell cancer comprising cells having at least one phenotype selected for the group consisting of OAcGD2$^+$/CD34$^+$/CD38$^-$, OAcGD2$^+$/CD34$^+$/CD19$^-$, OAcGD2$^+$/CD34$^+$/CD19$^+$, OAcGD2$^+$/CD34$^+$/CD38$^+$/CD19$^+$, OAcGD2$^+$/CD34$^+$/CD38$^-$/CD19$^+$, OAcGD2$^+$/CD133$^+$/CD38$^-$, OAcGD2$^+$/CD133$^+$/CD19$^-$, OAcGD2$^+$/interleukin-3-receptor $\alpha^+$, OAcGD2$^+$/CD33$^+$, OAcGD2$^+$/CD44$^+$/CD24$^{-/low}$, OAcGD2$^+$/CD44$^+$/CD24$^{-/low}$/ESA$^+$, OAcGD2$^+$/CD44$^+$/CD24$^{-/low}$/lin$^-$/ALDH1$^+$, OAcGD2$^+$/CD133$^+$, OAcGD2$^+$/A2B5$^+$, OAcGD2$^+$/SSEA-1$^+$, OAcGD2$^+$/CD133$^+$/ESA$^{high}$/CD44$^+$, OAcGD2$^+$/CD166$^+$, OAcGD2$^+$/CD26$^+$, OAcGD2$^+$/CD44$^+$/CD133$^+$/$\alpha 2\beta 1^+$, OAcGD2$^+$/CD44$^+$, OAcGD2$^+$/Sca$^+$/CD45$^-$/Pecam$^-$/

CD34+, OAcGD2+/ALDH1+/Oct4+/CD133+/ABCG2+/ CXCR4+, OAcGD2+/CD133+/CD44+, OAcGD2+/Ep-CAM+/AFP+, OAcGD2+/EMA−/CD44v6+, or OAcGD2+/ CD133+/CD44+/ALDH1+, wherein said kit comprises an anti-OAcGD2 antibody comprising a heavy chain variable region comprising SEQ ID NO:7 and a light chain variable region comprising SEQ ID NO:8 and instruction for use.

In a more particular embodiment, the kit may further comprises at least one antibody specific for at least one CSC biomarker as recited in table 1.

EXAMPLES

In the following, the invention is described in more detail with reference to amino acid sequences, nucleic acid sequences and examples. However, no limitation of the invention is intended by the details of the examples. Rather, the invention pertains to any embodiment which comprises details which are not explicitly mentioned in the examples herein, but which the skilled person finds without undue effort.

Gliomas

Evaluation of the Expression of OAcGD2 Ganglioside in Glioma

OAcGD2 Expression in Glioblastomas' Biopsies

The inventors evaluated the expression of the O-acetylated GD2 ganglioside (OAcGD2) in 22 glioblastoma samples using immunohistochemistry (IHC). An example of immunohistochemical staining for diagnosis is shown in FIG. 1, where tissues are stained for the OAcGD2 antigen.

Samples of tumors (glioblastomas) were obtained from surgical excision. A tissue sample (volume ≤0.5 cm3) was removed and frozen in isopentane cooled to the temperature of liquid nitrogen. After 60 seconds, the sample was removed and transferred and kept at −70° C. Sections of 10 µm were performed using a cryostat. Sections were collected on glass slides SUPERFROST GOLD+(VWR) and air-dried for 3 minutes. They were then fixed in acetone (−20° C.) for 10 minutes and air-dried again. The sections were then stored at −20° C. until use.

Antibody 8B6 Immunoreactivity was detected by stepwise incubation with a biotinylated-goat anti-mouse antibody, followed by streptavidin-biotin-peroxydase complex and DAB substrate. Specimen were analyzed by a pathologist with a light microscopic equipment and classified as negative, 1+, 2+ or 3+, compared to a human neuroblastoma frozen section as positive control, and tissue incubated with a irrelevant IgG3 antibody as negative control. Results are summarized in the Table 2.

TABLE 2

| Sample number | Score | % of OAcGD2+ tumor cells |
|---|---|---|
| 5 | 1+ | ND |
| 14 | 2+ | 100 |
| 3 | 3+ | 100 |

(ND: Not determined)

They found that all samples stained positively with anti-OAcGD2 monoclonal antibody (mAb) 8B6, with an IHC score ranging from 1+ to 3+. For 16 samples among 22, 100% tumor cells were positive within the tumor.

OAcGD2 Expression in Glioma Cell Lines and Primary Cells

Expression profiles of CD133 and OAcGD2 in U87MG human glioblastoma cells were determined by flow cytometry analysis. Cells were stained with the parent mouse mAb 8B6 specific for OAcGD2 and with CD133-FITC antibody. Cells were washed 3 times in ice-cold PBS, incubated with mAb 8B6 (10 µg/ml in PBS-BSA 1%) for 30 minutes at 4° C. After 3 washes in ice-cold PBS, primary bound antibody were detected with the F(ab)'$_2$ fragment of goat anti-mouse secondary antibody conjugated with FITC for 30 minutes. After washing, the cells were then incubated with CD133-APC conjugated antibody for 30 minutes at 4° C. After washing the cells 3 times with ice-cold PBS, cells were analyzed with a FACSCalibur cytometer (BD) using Cell Quest Pro software (BD). An isotype-matching antibody was used as negative control. At least $1 \times 10^4$ events were measured in cell lines.

Figure 2:
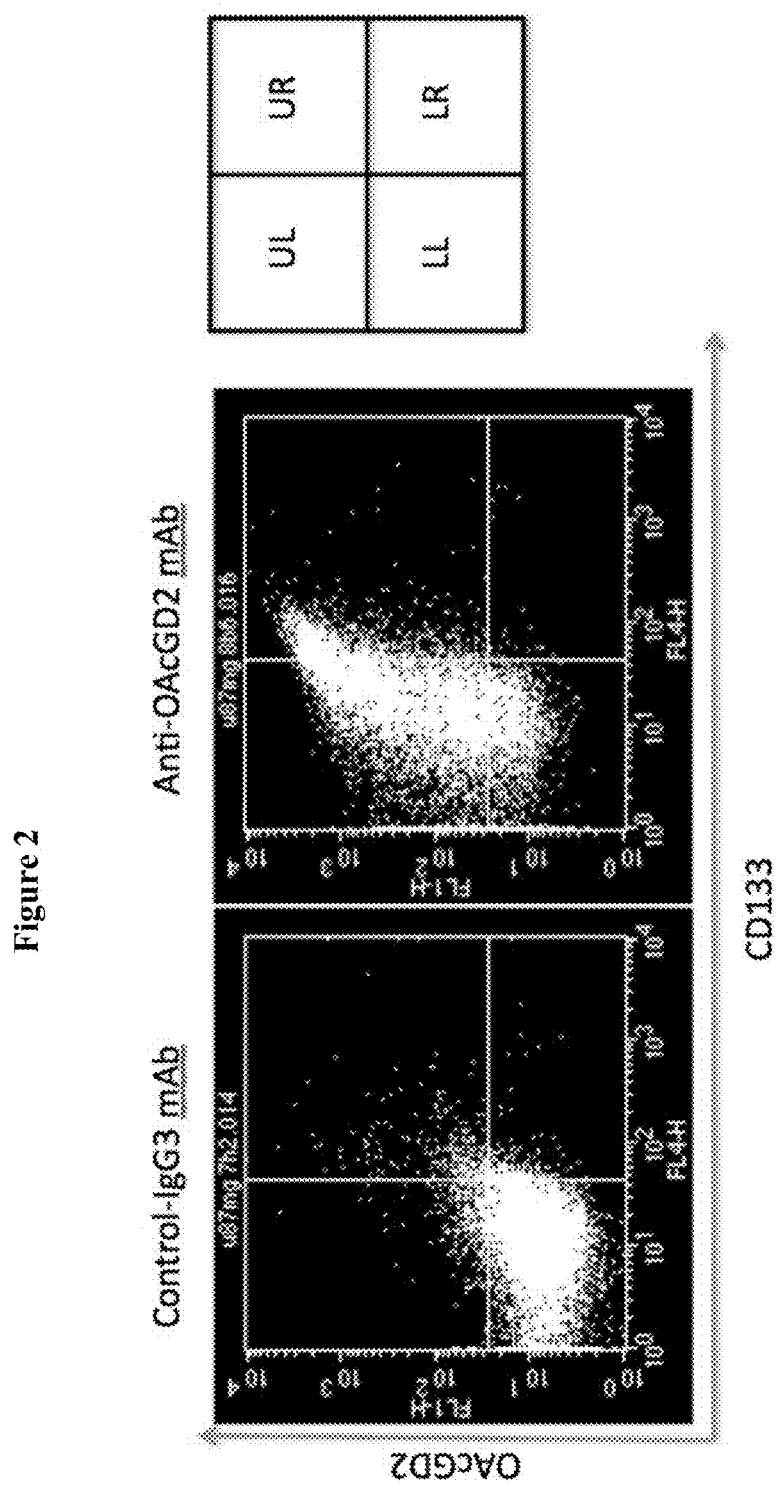
FIG. 2: OAcGD2 identifies CD133$^+$ stem cell phenotype in human glioblastoma cancer cells. UL, upper left quadrant, OAcGD2$^+$ U87MG human glioblastoma cells; UR, upper right quadrant, CD133$^+$ OAcGD2$^+$ U87MG human glioblastoma cells; LL, lower left quadrant, CD133$^-$ OAcGD2$^-$ U87MG human glioblastoma cells; LR, lower right quadrant, CD133$^+$ U87MG human glioblastoma cells.

Using flow cytometry, the inventors also detected OAcGD2 antigen at the cell surface of human glioma cell lines (3/3) and human primary glioma cells (12/12). For the human glioma cell lines, the rate of OAcGD2-positive cells ranged from 61 to 85% (FIG. 2, Table 3).

They also observed the presence of CD133+OAcGD2+ CSCs in these glioma cell lines, and within the CD133-positive cells, the rate of OAcGD2-positive cells was about 85 to 98%.

For the human primary glioma cells, the rate of OAcGD2-positive cells ranged from 32 to 94%. They also observed the presence of CD133+OAcGD2+ CSCs in these primary glioma cells, and within the CD133-positive cells, the rate of OAcGD2-positive cells was about 62 to 100% (Table 3).

TABLE 3

OAcGD2+, CD133+ and OACGD2+CD133+ (percentage of OAcGD2+ cells among CD133+ cells) populations in glioma cells.

| Flux Cytometry | NAME | % population: OAc-GD2+ | % population: CD133+ | % population++: (OAc-GD2+CD133+)/ pop. tot. CD133+ × 100 | % OAcGD2 dans pop CD133− |
|---|---|---|---|---|---|
| PRIMARY CELLS | AMBMa | 75% | 15.4% | 96.2% | 71.2% |
| | BROJa | 68% | 50.55% | 91.4% | 44.1% |
| | CoxCa | 55.55% | 27.4% | 91.8% | 41.9% |
| | DONGu | 40.2% | 14.1% | 71.1% | 35.2% |
| | DuGan | 59.9% | 34.8% | 94.4% | 41.5% |
| | HouHe | 29.2% | 28.4% | 61.7% | 16.3% |
| | BAuJe | 94.6% | 18.55% | 99.8% | 93.4% |
| | BICyv | 84.05% | 8.2% | 97.8% | 82.8% |
| | CAuMi | 79.15% | 5.05% | 100% | 78% |
| | DuASO | 88.8% | 11.9% | 100% | 87.3% |
| | GBMA1 | 54% | 7.9% | 90.9% | 50.8% |
| | HARCi | 69.9% | 6.2% | 99.7% | 67.9% |

TABLE 3-continued

OAcGD2+, CD133+ and OACGD2+CD133+ (percentage of OAcGD2+ cells among CD133+ cells) populations in glioma cells.

| Flux Cytometry | NAME | % population: OAc-GD2+ | % population: CD133+ | % population++: (OAc-GD2+CD133+)/ pop. tot. CD133+ × 100 | % OAcGD2 dans pop CD133− |
|---|---|---|---|---|---|
| CELL LINES | LN-18 | 84.1% | 11% | 94.1% | 82.9% |
| | U251 | 46.5% | 1.4% | 84.9% | 46% |
| | U87-MG | 81.3% | 14.9% | 98.3% | 78.4% |

The results confirm those obtained on glioblastomas' biopsies with a strong OAcGD2 expression in gliomas's primary cell and also in glioma cell lines. Moreover, the search of CSC (CD133+) among these gliomas' primary cells and also glioma cell lines has enabled the identification of various percentage of such CSC (CD133+). Now, and surprisingly, the results have shown that OAcGD2 expression is enriched in these CSC as compared to non CSC. As an example, the percentage of positive OAcGD2 cells was two fold greater for CSC than for non CSC (data not shown).

Finally, the results established that OAcGD2 is enriched in gliomas' CSC and can be used for facilitating the targeting of these cells.

OAcGD2 Expression in Glioblastoma (GBM) Cells and in Glioblastoma Stem Cells (GSC)

Analysis of OAcGD2 expression in GBM cells was performed by indirect immunofluorescence measured by flow cytometry. Cells were washed with cold PBS, fixed with PFA 4% (Electron Microscopy Sciences, Hatfield, Pa.) for 10 min at 4° C., and then incubated with mAb 8B6 (10 µg/ml) for 45 min. Antibody 8B6 binding was detected by incubation with a fluorescein isothiocyanate-labeled F(ab')2 fragment of goat anti-mouse IgG (Jackson Immunoresearch, Soham, UK) for 60 min at 4° C. Separate experiments were performed with the control IgG. For OAcGD2 expression analysis in glioblastoma stem cells (GSCs), GBM neurospheres were dissociated and dissociated cells were permeabilized with saponin solution 0.5% (Sigma Aldrich, St. Louis, Mo.) for 10 min. Cells were then incubated with 10 µg/ml of PE-labeled anti-human CD133/1 (clone: AC133, Milltenyi, Bergisch Gladbach, Germany), V450-labeled anti-human Nestin (clone 25, BD biosciences, Franklin Lakes, N.J.), or Alexa-Fluor 647 anti-human Sox 2 (Clone 245610, BD bioscience) in the presence of anti-OAcGD2 mAb 8B6 as describe above. Separate experiments were performed with appropriate isotype control antibodies. In both set of experiments, cell fluorescence was analyzed using a FACSCanto flow cytometer (BD Biosciences, San Jose, Calif., USA) and the FlowJo software (Flowjo LLC, Oregon, Oreg., USA).

The inventors studied OAcGD2 expression in GSC-containing GBM patient-derived cells. GBM10 is a primary culture isolated from a patient biopsy. Thus, they analyzed the binding of anti-OAcGD2 mAb binding on either CD133⁻ or Nestin-positive GBM cells. Indeed, GBM-10 expressed CD133 and Nestin stem cell markers. Of even greater interest, the inventors observed that both the CD133+ and the Nestin+ cell populations expressed high level of OAcGD2 (FIGS. 7A and 7B).

These results are similar to those obtained in table 3. In the GSC-containing GBM patient-derived cells, the rate of OAcGD2-positive cells was about 90%. The rate of CD133- positive cells was about 69.86%. And the rate of OAcGD2-positive cells within the CD133-positive cells was about 99.2%. In other words, the cells having the phenotype OAcGD2+/CD133+ represent 99.2% of the GSCs.

Nestin (Neuronal Stem cell protein), a class VI intermediate filament protein, was originally detected in neural stem cells during development. Increased nestin expression is typical for tumors generated from undifferentiated precursor cells or immature progenitors, which rapidly proliferate during neurogenesis. Nestin was detected in neuroectodermal neuroepithelial tumors, including tumors of astrocytic, oligodendroglial, oligoastrocytic, ependymal, embryonic, neuronal, and mixed neuronal-glial origin. Furthermore, nestin expression was found in mesenchymal tumors (e.g. osteosarcoma, rhabdomyosarcoma, gastrointestinal stromal tumor), germ cell tumors (e.g. embryonal carcinoma, germinoma, choriocarcinoma, yolk sac tumor), and epithelial tumors (e.g. pancreatic adenocarcinoma, breast carcinoma, ovarian carcinoma, lung carcinoma).

As illustrated in FIG. 7B, in the GSC-containing GBM patient-derived cells, the rate of OAcGD2-positive cells was about 90.2%. The rate of Nestin-positive cells was about 79.8%. And the rate of OAcGD2-positive cells within the Nestin-positive cells was about 97%. In other words, the cells having the phenotype OAcGD2+/CD133+ represent 97% of the GSCs.

Effects of 8B6 mAb on OAcGD2 Expressing Glioma Cells.

U87-MG tumor cells ($5 \times 10^5$ cells) were seeded in flat bottom 12-well plates and incubated with either mAb 8B6 or control-IgG3 antibody for 24 hours at 37° C., 5% CO2. Cell cultures were imaged with a LEICA DFC295 digital camera coupled to a LEICA 164 microscope.

After 24 hours incubation period, apoptotic cells assessed by morphological changes were observed under a phase-contrast microscope with the same magnification ×200. Arrow indicates apoptotic cell.

Figure 3:
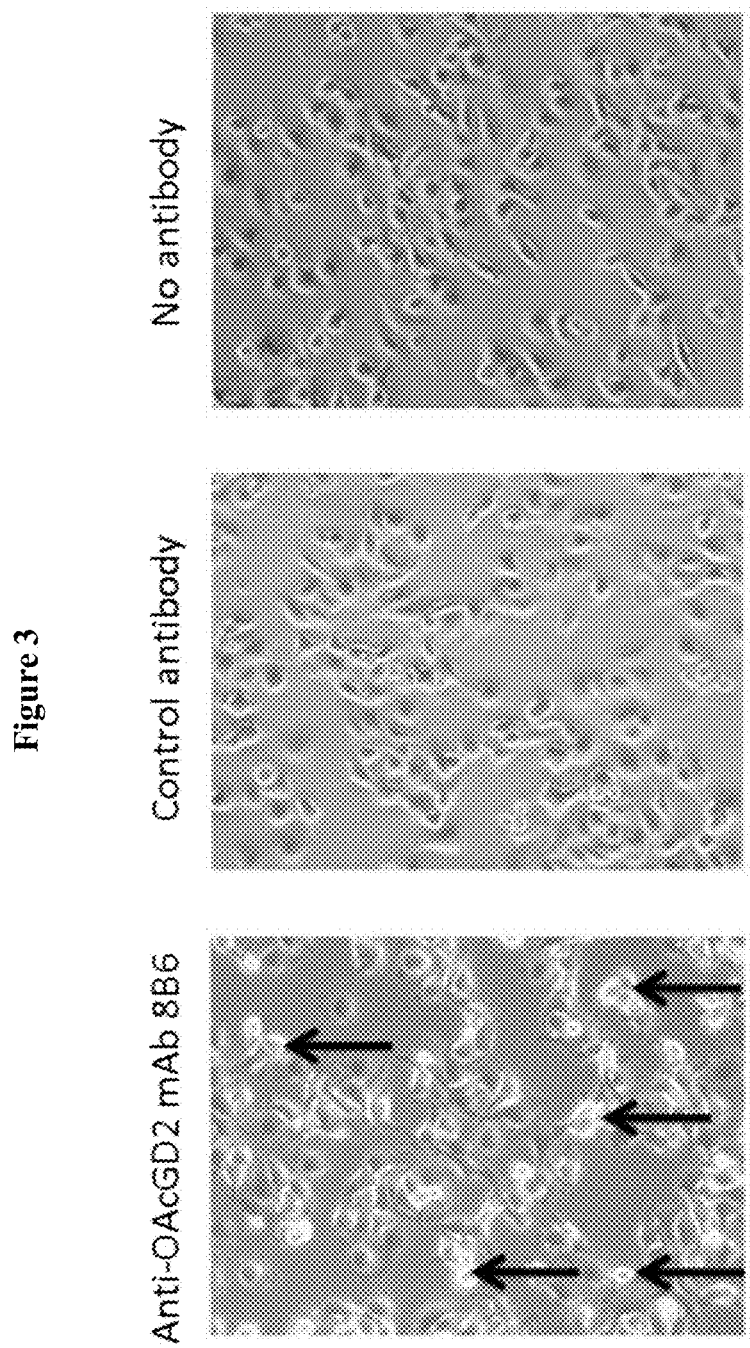
FIG. 3: Phase-contrast microscopic examination of U87MG human glioblastoma cells exposed to 50 µg/ml of either control antibody or mAb 8B6. After 24 hours incubation period, apoptotic cells assessed by morphological changes were observed under a phase-contrast microscope with the same magnification ×200. Arrow indicates apoptotic cell.

Treatment with mAb 8B6 induced change in U87MG cell morphology. Cells incubated with mAb 8B6 a spherical shape and formed blebs, which were either loosely attached to the bottom of the culture vessel or floating in the culture media. The cells segregated into several fragments with are characteristic of apoptosis (FIG. 3). Among the U87-MG cells, it can be speculated that the CSC, which cells expressed the highest percentage of OAcGD2, die following apoptosis.

Effects of 8B6 mAb on Glioblastoma in an In Vivo Model

Female nude (nu/nu) athymic mice (Harlan Laboratories) were cared for and maintained in accordance with applicable European Animal Welfare regulations under an approved Institutional Animal Care and Use Protocol in an animal facility at University of Nantes accredited by the French Department of agriculture.

Aliquots of U251 cell suspension ($3 \times 10^6$ cell/100 µl containing an equal volume of RPMI and matrigel) were implanted subcutaneously on the left flank of mice. A week later the tumor mass was present in all the originally injected mice which were then randomized into three equal groups and antibody treatment was started. Anti-OAcGD2 mAb 8B6 was formulated as a phosphate-buffered saline solution and injected intravenously. One group was treated with one injection of 500 µg mAb 8B6 while the control group was treated with an equal volume of PBS alone as the vehicle. The third group was treated with an isotype-matching mAb as negative control. Tumors were measured by calipers; the tumor volume was calculated according to the formula length×width$^2$×π/6.

Figure 4:
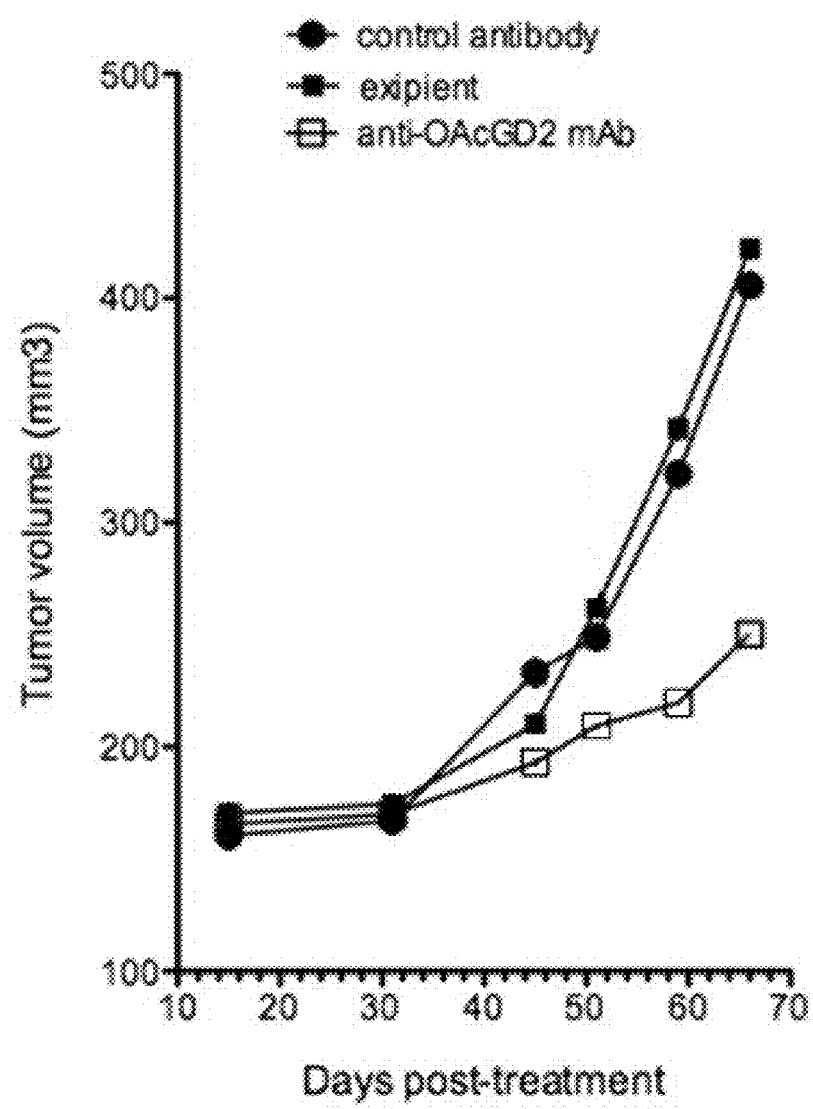
FIG. 4: Anti-OAcGD2 mAb inhibits human glioblastoma tumor growth in mice.

The inventors also found that anti-OAcGD2 mAb inhibits human glioblastoma tumor growth in mice (FIG. 4). When the tumor volume reached 100 mm$^3$, the mice were injected with either 500 µg of mAb 8B6 or control-IgG3 mAb and the tumor growth was followed. Antibody 8B6 inhibited human U251 glioblastoma tumor growth compared to the vehicle- and the control IgG3-treated mice. Sixty-eight days after antibody injection, tumor volumes averaged 423±236 mm$^3$ and 405±176 mm$^3$ in the vehicle- and the control IgG3-treated groups, respectively. In contrast, mAb 8B6 treatment inhibited U251 tumor growth with an average tumor volume of 254±142 mm$^3$. The specificity of the treatment was demonstrated since treatment with an equivalent amount of non-specific IgG3 antibody was remains ineffective. Finally, it was demonstrated that no CSC can be identified in mice treated with 8B6 as compared to IgG3-treated mice (data not shown).

In conclusion, the results established that anti-OAcGD2 antibody has enabled to eliminate CSC cells in vivo, this elimination being associated with a clear and strong inhibition of tumor growth.

Breast Cancers

Evaluation of the Expression of OAcGD2 Ganglioside in Breast Cancer

OAcGD2 Expression in Breast Cancer Tissues

The inventors have performed preliminary immunohistochemistry to evaluate the expression of OAc-GD2 in fixed-formalin paraffin-embedded cancer tissues with the 8B6 monoclonal antibody.

Now, they established that among 25 stained breast cancer biopsies, 18 samples stained positively, with 1 sample showing faint staining (score 1+), 9 samples showing moderate staining (score 2+), and 8 samples showing strong staining (score 3+).

This strong correlation between breast cancer tissue and OAcGD2 was confirm by other immunochemistries performed on 28 frozen sections of other breast cancer tissues. For this series of experimentation, all samples stained positively for OAcGD2.

Consequently, it seems that OAcGD2 can be sued as a marker of breast cancer.

OAcGD2 Expression in Breast Cancer Cell Lines

The OAcGD2 expression has been evaluated in the breast cancer cell line SUM159. Expression profile of OAcGD2 in human breast cancer stem cells was determined by flow cytometry analysis after a triple fluorescent staining. Cells were incubated with the primary antibodies 8B6, 14G2a and 7H2 (at 10 µg/ml) for 45 minutes on ice in PBS-BSA 1%. After 3 washes in ice-cold PBS, primary bound antibody were detected with the Alexa Fluor® 568 Goat Anti-Mouse IgG (H+L) (Life Technologies) for 45 minutes on ice. Next, cells were fixed to PFA 4% for 10 minutes and then incubated for 25 minutes with anti-CD24 conjugate with FITC and anti-CD44 conjugated with APC (BD). After washing, cells were analyzed with a LSRII flow cytometer (BD) using FlowJo software (BD). At least 1×10$^4$ events were measured in cell lines.

It was found that approximately 35% of the cells expressed OAcGD2 (8B6 antibody), while only nearly 15% expressed GD2 ganglioside (14G2a antibody). Such a different expression was confirmed in another breast cancer cell lines (HMLE, data not shown). Then, we evaluated the proportion of CD44$^+$CD24$^{-/low}$ cells of within the cell line SUM159, and show that 94% of the cells exhibit a CSCs phenotype. If the percentage of OAcGD2 positive cells among CSC as compared to non-CSC was not determined in SUM159, such percentage was shown to be 5 fold greater in another breast cancer cell lines (HMLE, data not shown). Thus, and as for the results obtained in gliomas, it seems that OAcGD2 is enriched in breast cancers' CSC and can be used for facilitating the targeting of these cells. Moreover, these results are very interesting since they enable to envisage a therapeutic efficiency of a treatment targeting OAcGD2 in contrast to a treatment targeting GD2. In fact, targeting the few percentage of GD2 expressing cells does not ensure to limit the propagation of the associated cancer.

Viability Inhibition of the Breast Cancer Cells with 8B6 Antibody

The inventors performed a cell proliferation assay with anti-OAcGD2 and anti-GD2 antibodies on the breast cancer SUM159 cell line.

10$^4$ SUM159 cells (100 µL) were incubated in a 96-well microplate 24 h at 37° C. Antibodies from 80-1.25 µg/mL in 50 µL medium were added and incubated 24 h at 37° C. Fifty µg of MTT were added to each well and incubated at least 4 h at 37° C., before cells were solubilized with 10% SDS to stop the cellular conversion of the MTT dye and incubated O.N. at 37° C. The absorbance was then read at 570 and 650 nm. Absorbance of the product at 650 nm was subtracted from the absorbance at 570 nm (Abs$_{570}$–Abs$_{650}$) to calculate total conversion of dye. Four control wells with cells treated with 20 µg etoposide provide the blank for absorbance giving the 0% of viability. The viability (%) was expressed as a percentage relative to the untreated cells and each value is represented as mean±SEM in quadruplicate.

Figure 5:
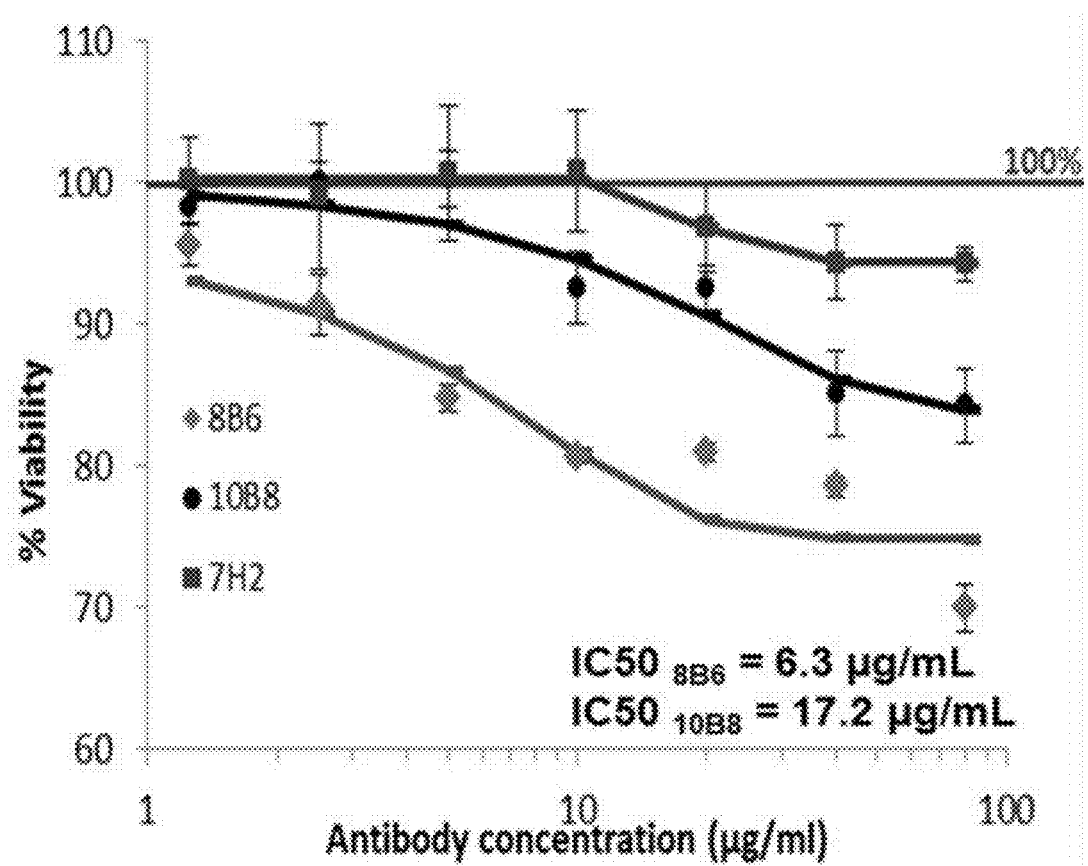
FIG. 5: Cytotoxicity of anti-GD2 and anti-OAcGD2 antibodies on breast cancer cells. Direct cytotoxicity is evaluated by MTT assay with increasing concentrations the murine anti-GD2 (10B8) and anti-OAcGD2 (8B6) antibodies.

The 8B6 antibody induced direct cytotoxicity on this cell line approaching 30% of viability inhibition (FIG. 5).

Lung Cancers

Evaluation of the Expression of OAcGD2 Ganglioside in Small Cell Lung Cancer

OAcGD2 Expression in Lung Cancer Cell Lines

The OAcGD2 expression has been evaluated in the lung cancer cell line H196. Expression profile of OAcGD2 in human lung cancer stem cells was determined by flow cytometry analysis after a double fluorescent staining. Cells were incubated with the primary antibodies 8B6, 10B8 and 7H2 (at 10 µg/ml) for 45 minutes on ice in PBS-BSA 1%. After 3 washes in ice-cold PBS, primary bound antibody were detected with the FITC conjugated Goat Anti-Mouse IgG (H+L) (JacksonResearch) for 45 minutes on ice. Next, cells were fixed to PFA 4% for 10 minutes and then incubated for 25 minutes with anti-CD133 conjugate with APC (Miltenyi Biotec). After washing, cells were analyzed with a FACScalibur flow cytometer (BD) using CellQuest software (BD). At least 1×10$^4$ events were measured in cell lines.

Figure 6:
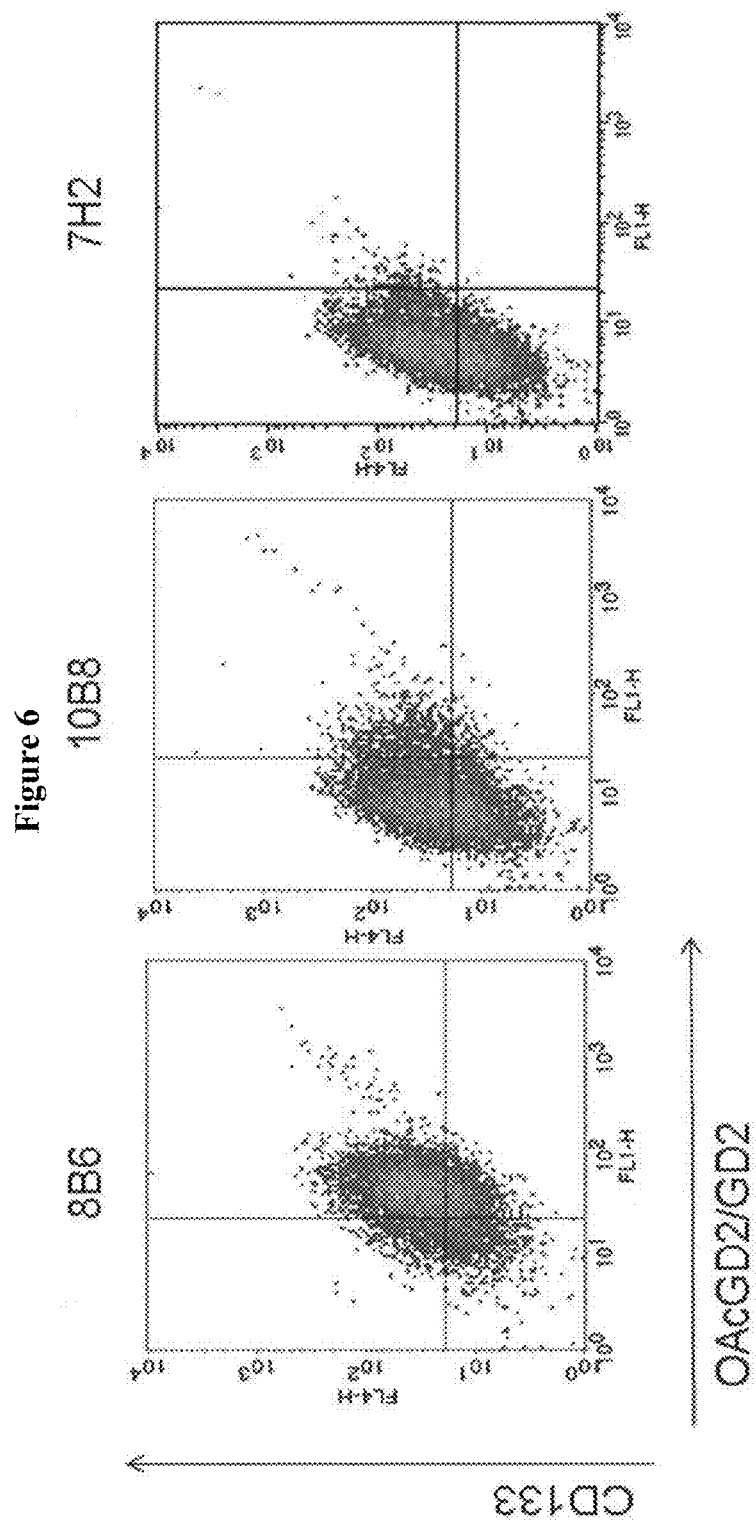
FIG. 6: Expression of OAcGD2 in CSC in small cell lung cancer. Expression profiles in flow cytometry for H196 cells lines of CD133 (CSC) simultaneously with OAcGD2 (8B6) or GD2 (10B8).

The results are presented in FIG. 6.

Again, the results show that the expressions of OAcGD2 and of CD133 were correlated with more than 50% of CSC cells expressing OAcGD2. The expression of GD2 in these cells was slightly greater than the negative control (i.e. 7%).

Again, it seems that OAcGD2 is enriched in small cell lung cancers' CSC and can be used for facilitating the targeting of these cells.

Leukemias

The inventors have performed preliminary indirect immunofluorescence assay to evaluate the expression of OAcGD2 in acute lymphoid leukemia (ALL) and acute myeloid leukemia (AML) with the 8B6 monoclonal antibody.

Two of the tested ALL cell lines were positive. One AML sample from a patient was also positive.

The co-expression of OAcGD2 ganglioside and at least one other CSC biomarkers as recited in table 1 were also assayed on other CSC cancers such as leukemia, colorectal cancer, pancreatic cancer, prostate cancer, liver cancer, bladder cancer or gastric cancer. Thus, and as for the results obtained in gliomas and breast cancer, it seems that OAcGD2 is enriched in cancer having CSC and can be used for facilitating the targeting of these cells.

The invention claimed is:

1. A method of detecting O-acetylated-GD2 ganglioside (OAcGD2) in a subject suspected of having a cancer stem cell (CSC) cancer, comprising:
   i) obtaining a biological sample comprising tumor cells from said subject;
   ii) detecting whether OAcGD2 is coexpressed with at least one CSC biomarker selected from the group consisting of:

| Cancer type | CSC biomarkers and/or phenotypes |
| --- | --- |
| Acute myeloid leukemia | $CD34^+/CD38^-$ |
|  | interleukin-3-receptor $\alpha^+$ |
|  | $CD33^+$ |
| Acute lymphoid leukemia | $CD34^+/CD19^+$ |
|  | $CD34^+/CD19^-$ |
|  | $CD34^+/CD38^+/CD19^+$ |
|  | $CD34^+/CD38^-/CD19^+$ |
|  | interleukin-3-receptor $\alpha^+$ |
|  | $CD33^+$ |
|  | $CD133^+/CD38^-$ |
|  | $CD133^+/CD19^-$ |
| Breast cancer | $CD44^+/CD24^{-/low}$ |
|  | $CD44^+/CD24^{-/low}/ESA^+$ |
|  | $CD44^+/CD24^{-/low}/lin^-/ALDH1^+$ |
| Glioma cancer | $CD133^+$ |
|  | $A2B5^+$ |
|  | $SSEA-1^+$ |
| Colorectal cancer | $CD133^+/ESA^{high}/CD44^+$ |
|  | $CD166^+$ |
|  | $CD26^+$ |
| Pancreatic cancer | $CD133^+$ |
|  | $CD44^+/CD24^+/ESA^+$ |
| Prostate cancer | $CD44^+/CD133^+/\alpha2\beta1^+$ |
|  | $CD44^+$ |
| Lung cancer | $Sca^+/CD45^-/Pecam^-/CD34^+$ |
|  | $ALDH1^+/Oct4^+/CD133^+/ABCG2^+/CXCR4^+$ |
| Liver cancer | $CD133^+/CD44^+$ |
|  | $EpCAM^+/AFP^+$ |
| Bladder cancer s | $EMA^-/CD44v6^+$ |
| Gastric cancer | $CD133^+/CD44^+$ |
|  | $CD44^+$, $CD133^+/CD44^+/ALDH1^+$ | at the surface of CSC by contacting the biological sample with an anti-OAcGD2 antibody and with at least one antibody specific for the at least one CSC biomarker and detecting binding between OAcGD2 and the corresponding antibody and between the at least one CSC biomarker and the corresponding antibody, wherein the anti-OAcGD2 antibody comprises a heavy chain variable region comprising SEQ ID NO:7 and a light chain variable region comprising SEQ ID NO:8.

2. The method of claim 1, wherein the anti-OAcGD2 antibody bind the O-acetylated-GD2 ganglioside with an affinity of less than $10^{-7}$ M.

3. The method of claim 1, wherein the anti-OAcGD2 antibody is labelled with a fluorophore, chromophore, radioelement, enzyme or conjugated with a substrate or with the protein or ligand of a protein of a protein/ligand pair.

4. The method of claim 1, wherein the detecting is by a method based on enzyme immunoassay (EIA), radioimmunoassay (RIA), Western blot analysis, enzyme linked immunoabsorbant assay (ELISA), Immuno Thin Layer Chromatography (ITLC), flow cytometry or FACS.

5. The method of claim 1, wherein at least 10% of cancer stem cells (CSC) express the O-acetylated-GD2 ganglioside.

6. The method of claim 1, wherein CSC have at least one phenotype selected from the group consisting of: $OAcGD2^+/CD34^+/CD38^-$, $OAcGD2^+/CD34^+/CD19^-$, $OAcGD2^+/CD34^+/CD19^+$, $OAcGD2^+/CD34^+/CD38^+/CD19^+$, $OAcGD2^+/CD34^+/CD38^-/CD19^+$, $OAcGD2^+/CD133^+/CD38^-$, $OAcGD2^+/CD133^+/CD19^-$, $OAcGD2^+$/interleukin-3-receptor $\alpha^+$, $OAcGD2^+/_{CD}33^+$, $OAcGD2^+/_{CD}44^+/CD24^{-/low}$, $OAcGD2^+/CD44^+/CD24^{-/low}/ESA^+$, $OAcGD2^+/CD44^+/CD24^{-/low}/lin^-/ALDH1^+$, $OAcGD2^+/CD133^+$, $OAcGD2^+/A2B5^+$, $OAcGD2^+/SSEA-1^+$, $OAcGD2^+/CD133^+/ESA^{high}/CD44^+$, $OAcGD2^+/CD166^+$, $OAcGD2^+/CD26^+$, $OAcGD2^+/CD44^+/CD133^+/\alpha2\beta1^+$, $OAcGD2^+/CD44^+$, $OAcGD2^+/Sca^+/CD45^-/Pecam^-/CD34^+$, $OAcGD2^+/ALDH1^+/Oct4^+/CD133^+/ABCG2^+/CXCR4^+$, $OAcGD2^+/CD133^+/CD44^+$, $OAcGD2^+/EpCAM^+/AFP^+$, $OAcGD2^+/EMA^-/CD44v6^+$, and $OAcGD2^+/CD133^+/CD44^+/ALDH1^+$.

7. The method of claim 6, wherein CSC have the phenotype $OAcGD2^+/CD44^+/CD24^{-/low}$, $OAcGD2^+/CD44^+/CD24^{-/low}/ESA^+$, or $OAcGD2^+/CD44^+/CD24^{-/low}/lin^-/ALDH1^+$.

8. The method according to claim 1; wherein the biological sample is obtained from a solid tumor or a blood sample.

9. The method of claim 1, wherein the anti-OAcGD2 antibody binds the O-acetylated-GD2 ganglioside with an affinity of less than $5 \times 10^{-8}$ M.

10. The method of claim 1, wherein the anti-OAcGD2 antibody binds the O-acetylated-GD2 ganglioside with an affinity of less than $10^{-8}$ M.

11. The method of claim 1, wherein at least 30% of cancer stem cells (CSC) express the O-acetylated-GD2 ganglioside.

12. The method of claim 1, wherein at least 50% of cancer stem cells (CSC) express the O-acetylated-GD2 ganglioside.

* * * * *

SEQUENCE LISTING

```
<160> NUMBER OF SEQ ID NOS: 10

<210> SEQ ID NO 1
<211> LENGTH: 12
<212> TYPE: PRT
<213> ORGANISM: Mus musculus

<400> SEQUENCE: 1

Gln Ser Leu Leu Lys Asn Asn Gly Asn Thr Phe Leu
1               5                   10

<210> SEQ ID NO 2
<211> LENGTH: 3
<212> TYPE: PRT
<213> ORGANISM: Mus musculus

<400> SEQUENCE: 2

Lys Val Ser
1

<210> SEQ ID NO 3
<211> LENGTH: 9
<212> TYPE: PRT
<213> ORGANISM: Mus musculus

<400> SEQUENCE: 3

Ser Gln Ser Thr His Ile Pro Tyr Thr
1               5

<210> SEQ ID NO 4
<211> LENGTH: 8
<212> TYPE: PRT
<213> ORGANISM: Mus musculus

<400> SEQUENCE: 4

Glu Phe Thr Phe Thr Asp Tyr Tyr
1               5

<210> SEQ ID NO 5
<211> LENGTH: 10
<212> TYPE: PRT
<213> ORGANISM: Mus musculus

<400> SEQUENCE: 5

Ile Arg Asn Arg Ala Asn Gly Tyr Thr Thr
1               5                   10

<210> SEQ ID NO 6
<211> LENGTH: 10
<212> TYPE: PRT
<213> ORGANISM: Mus musculus

<400> SEQUENCE: 6

Ala Arg Val Ser Asn Trp Ala Phe Asp Tyr
```

<210> SEQ ID NO 7
<211> LENGTH: 112
<212> TYPE: PRT
<213> ORGANISM: Mus musculus

<400> SEQUENCE: 7

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110
```

<210> SEQ ID NO 8
<211> LENGTH: 119
<212> TYPE: PRT
<213> ORGANISM: Mus musculus

<400> SEQUENCE: 8

```
Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser
        115
```

<210> SEQ ID NO 9
<211> LENGTH: 112
<212> TYPE: PRT
<213> ORGANISM: Artificial Sequence
<220> FEATURE:
<223> OTHER INFORMATION: Chimeric antibody chain

<400> SEQUENCE: 9

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30
```

-continued

```
Asn Gly Asn Thr Phe Leu His Trp Tyr Leu Gln Lys Ser Gly Gln Ser
            35                  40                  45
Pro Lys Leu Leu Ile Tyr Lys Val Ser Asn Arg Leu Ser Gly Val Pro
 50                      55                  60
Asp Arg Phe Ser Gly Ser Gly Ser Gly Thr Tyr Phe Thr Leu Lys Ile
 65                  70                  75                  80
Ser Arg Val Glu Ala Glu Asp Leu Gly Val Tyr Phe Cys Ser Gln Ser
                 85                  90                  95
Thr His Ile Pro Tyr Thr Phe Gly Gly Gly Thr Lys Leu Glu Ile Lys
                100                 105                 110

<210> SEQ ID NO 10
<211> LENGTH: 119
<212> TYPE: PRT
<213> ORGANISM: Artificial Sequence
<220> FEATURE:
<223> OTHER INFORMATION: Chimeric antibody chain

<400> SEQUENCE: 10

Glu Val Lys Leu Val Glu Ser Gly Gly Gly Leu Val Leu Pro Gly Asp
 1               5                  10                  15
Ser Leu Arg Leu Ser Cys Ala Thr Ser Glu Phe Thr Phe Thr Asp Tyr
            20                  25                  30
Tyr Met Thr Trp Val Arg Gln Pro Pro Arg Lys Ala Leu Glu Trp Leu
            35                  40                  45
Gly Phe Ile Arg Asn Arg Ala Asn Gly Tyr Thr Thr Glu Tyr Asn Pro
         50                  55                  60
Ser Val Lys Gly Arg Phe Thr Ile Ser Arg Asp Asn Ser Gln Ser Ile
 65                  70                  75                  80
Leu Tyr Leu Gln Met Asn Thr Leu Arg Thr Glu Asp Ser Ala Thr Tyr
                 85                  90                  95
Tyr Cys Ala Arg Val Ser Asn Trp Ala Phe Asp Tyr Trp Gly Gln Gly
                100                 105                 110
Thr Thr Leu Thr Val Ser Ser
            115
```